US011293025B2

(12) United States Patent
Rigo et al.

(10) Patent No.: US 11,293,025 B2
(45) Date of Patent: Apr. 5, 2022

(54) COMPOSITIONS AND METHODS FOR MODULATING ATAXIN 3 EXPRESSION

(71) Applicants: IONIS PHARMACEUTICALS, INC., Carlsbad, CA (US); ACADEMISCH ZIEKENHUIS LEIDEN, Leiden (NL)

(72) Inventors: Frank Rigo, Carlsbad, CA (US); Thazha P. Prakash, Carlsbad, CA (US); Wilhelmina Maria Clasina Van Roon-Mom, Leiden (NL); Lodewijk Julius Anton Toonen, Leiden (NL)

(73) Assignees: Ionis Pharmaceuticals, Inc., Carlsbad, CA (US); Academisch Ziekenhuis Leiden, Leiden (NL)

( * ) Notice: Subject to any disclaimer, the term of this patent is extended or adjusted under 35 U.S.C. 154(b) by 0 days.

(21) Appl. No.: 16/695,551

(22) Filed: Nov. 26, 2019

(65) Prior Publication Data

US 2020/0325473 A1 Oct. 15, 2020

Related U.S. Application Data

(63) Continuation of application No. 15/761,964, filed as application No. PCT/US2016/053416 on Sep. 23, 2016, now Pat. No. 10,533,175.

(60) Provisional application No. 62/315,521, filed on Mar. 30, 2016, provisional application No. 62/307,279, filed on Mar. 11, 2016, provisional application No. 62/232,956, filed on Sep. 25, 2015.

(51) Int. Cl.
*C12N 15/113* (2010.01)
*C12N 9/48* (2006.01)
*A61K 31/712* (2006.01)

(52) U.S. Cl.
CPC .......... *C12N 15/113* (2013.01); *A61K 31/712* (2013.01); *C12N 9/485* (2013.01); *C12Y 304/19012* (2013.01); *C12N 2310/11* (2013.01); *C12N 2310/321* (2013.01); *C12N 2310/3231* (2013.01); *C12N 2310/3341* (2013.01); *C12N 2310/3525* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,457,187 A | 7/1984 | Tsuboi |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,023,243 A | 6/1991 | Tullis |
| 5,013,830 A | 7/1991 | Ohutsuka et al. |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |

(Continued)

FOREIGN PATENT DOCUMENTS

| | | |
|---|---|---|
| JP | 2011125219 | 6/2011 |
| WO | WO2002/058626 | 8/2002 |

(Continued)

OTHER PUBLICATIONS

Alves et al., "Allele-Specific RNA Silencing of Mutant Ataxin-3 Mediates Neuroprotection in a Rat Model of Machado-Joseph Disease" PLoS One (2008) 3(10):e3341.

(Continued)

*Primary Examiner* — Tracy Vivlemore

(74) *Attorney, Agent, or Firm* — Barnes & Thornburg LLP

(57) ABSTRACT

Disclosed are methods for modulating splicing of Ataxin 3 mRNA in an animal with modified oligonucleotides. Such compounds and methods are useful to treat, prevent, or ameliorate spinocerebellar ataxia type 3 (SCA3) in an individual in need thereof.

24 Claims, 15 Drawing Sheets

Specification includes a Sequence Listing.

(56) References Cited

U.S. PATENT DOCUMENTS

| | | |
|---|---|---|
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | DeMesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,840,491 A | 11/1998 | Kakizuka |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,834,170 B2 | 11/2010 | Khvorova et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swazye et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,329,890 B2 | 11/2012 | Davidson et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,779,116 B2 | 7/2014 | Davidson et al. |
| 8,828,956 B2 | 9/2014 | Manoharan et al. |
| 8,901,095 B2 | 12/2014 | Corey et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rejeev et al. |
| 9,340,785 B2 | 5/2016 | Corey et al. |
| 9,487,779 B2 | 11/2016 | Davidson et al. |
| 9,574,191 B2 | 2/2017 | Corey et al. |
| 9,976,138 B2 | 5/2018 | Prakash et al. |
| 10,364,432 B2 | 7/2019 | Van Roon-Mom et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0244851 A1 | 11/2005 | Blume et al. |
| 2005/0272080 A1 | 12/2005 | Palma et al. |
| 2006/0148740 A1 | 7/2006 | Platenburg |

(56) References Cited

U.S. PATENT DOCUMENTS

| | | | |
|---|---|---|---|
| 2007/0031844 | A1 | 2/2007 | Khvorova et al. |
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2013/0130378 | A1 | 5/2013 | Manoharan et al. |
| 2013/0198877 | A1 | 8/2013 | Van Roon-Mom et al. |
| 2013/0225659 | A1 | 8/2013 | Bennett |
| 2014/0039037 | A1 | 2/2014 | Roon-Mom et al. |
| 2014/0107330 | A1 | 4/2014 | Freier et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0211006 | A1 | 7/2015 | Butler et al. |
| 2015/0267195 | A1 | 9/2015 | Seth et al. |
| 2015/0267197 | A1 | 9/2015 | Bennett et al. |
| 2015/0315595 | A1* | 11/2015 | Uzcategui ............... A61P 25/00 514/44 A |
| 2016/0159846 | A1 | 6/2016 | Prakash et al. |

FOREIGN PATENT DOCUMENTS

| | | |
|---|---|---|
| WO | WO2004013280 | 2/2004 |
| WO | WO 2004/045543 | 6/2004 |
| WO | WO 2006/006948 | 1/2006 |
| WO | WO2010014592 | 2/2010 |
| WO | 2011/097643 | 8/2011 |
| WO | WO2011/097388 | 8/2011 |
| WO | 2012/012467 | 1/2012 |
| WO | WO2012018257 | 2/2012 |
| WO | WO2013033223 | 5/2013 |
| WO | WO2013138353 | 9/2013 |
| WO | WO 2013/173635 | 11/2013 |
| WO | WO 2004/058940 | 7/2014 |
| WO | WO2015017675 | 2/2015 |
| WO | WO2015053624 | 4/2015 |
| WO | 2015/143246 | 9/2015 |
| WO | WO2017053781 | 3/2017 |
| WO | WO2018089805 | 5/2018 |
| WO | WO 2020/245233 | 12/2020 |

OTHER PUBLICATIONS

Alves et al., "Silencing ataxin-3 mitigates degeneration in a rat model of Machado-Joseph disease: no role for wild-type ataxin-3?" Hum. Mol. Gen. (2010) 19(12): 2380-2394.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Evers et al., "Ataxin-3 Protein and RNA Toxicity in Spinocerebellar Ataxia Type 3: Current Insights and Emerging Therapeutic Strategies." Mol Neurobiol (2014) 49:1513-1531.

Evers et al., "Ataxin-3 protein modification as a treatment strategy for spinocerebellar ataxia type 3: Removal of the CAG containing exon" Neurobiloby of Disease (2013) 58: 49-56.

Gautschi et al., "Activity of a novel bcl-2/bcl-xLbispecific antisense oligonucleotide against tumors of diverse histologic origins" J. Natl. Cancer Inst. (2001) 93:463-471.

Hu et al., "Allele-specific silencing of mutant huntingtin and ataxin-3 genes by targeting expanded CAG repeats in mRNAs." Nat. Biotech. (2009) 27(5): 478-484.

Hu et al., Allele-selective inhibition of ataxin-3 (ATX3) expression by antisense oligomers and duplex RNAs. Biol. Chem. (2011) 392(4): 315-325.

Kawaguchi et al., "CAG expansions in a novel gene for Machado-Joseph disease at chromosome 14q32.1." Nat. Genet. (1994) 8(3): 221-228.

Liu et al., "ss-siRNAs allele selectively inhibit ataxin-3 expression: multiple mechanisms for an alternative gene silencing strategy." Nucleic Acids Res. (2013) 41(20): 9570-9583.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Miller et al., "Allele-specific silencing of dominant disease genes." PNAS (2003) 100(12): 7195-7200.

Riess, et al., "SCA:3 Neurological features, patholgenesis and animal models." The Cerebellum (2008) 7:125-137.

Rodriguez-Lebron et al., "Silencing mutant ATXN3 expression resolves molecular phenotypes in SCA3 transgenic mice." Mol. Ther. (2013) 21(10): 1909-1918.

Seidel et al., "Axonal inclusions in spinocerebellar ataxia type 3." Acta Neuropathol (2010) 120:449-460.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Ward et al., "Ataxin-3, DAN damage repair, and SCA3 cerebellar degeneration: on the path to parsimony?" PLoS Genet (2015) 11(1):e1004937(1-4).

Woolf et al., "Specificity of antisense oligonucleotides in vivo" PNAS (1992) 89: 7305-7309.

PCT Search Report and Written Opinion for PCT/US2016-053416, completed Jan. 31, 2017.

Moore, et al., "Widespread In vivo suppression of mutant ATXN3 by antisense oligonucleotides in transgenic mouse models of SCA3," 2016, Society for Neuroscience 2016 Neuroscience meeting, San Diego, CA, Retrieved from the internet on Aug. 2, 2018, http://www.abstractsonline.com/pp8/#!/4071/presentation/6726.

Moore, et al., "Widespread In vivo suppression of mutant ATXN3 by antisense oligonucleotides in transgenic mouse models of SCA3," Society for Neuroscience 2016 Neuroscience meeting, San Diego, CA, Poster Presentation Nov. 12, 2016.

Toonen, et al., "Ataxin-3 exon skipping as a treatment strategy for Spinocerebellar Ataxia type 3" Oligonucleotide Therapeutics Society 2015 Annual Meeting, Leiden, The Netherlands, Poster Presentation, Oct. 11, 2015.

Toonen, et al., "Antisense Oligonucleotide-Mediated Removal of the Polyglutamine Repeat in Spinocerebellar Ataxia Type 3 Mice." Mol. Therapy: Nucleic Acids (2017) 8:232-242.

McLoughlin, et al., "Oligonucleotide therapy mitigates disease in Spinocerebellar Ataxia Type 3 mice." Annals of Neurology (2018) Accepted Article online Jun. 16, 2018, pp. 1-25.

Yu, Dongbo "Single-Stranded RNAs Use RNAi to Potently and Allele-Selectively Inhibit Mutant Huntingtin Expression," Cell. Aug. 31, 2012; 150(5): pp. 895-908.

Hu, Jiaxin "Allele-selective inhibition of huntingtin expression by switching to an miRNA-like RNAi mechanism," Chem. Biol. Nov. 24, 2011, 17(11): pp. 1183-1188.

"SiRNA-optimized Modifications for Enhanced In Vivo Activity," by Denise M. Kenski et al.; Molecular Therapy-Nucleic Acids (2012) 1, e5; doi:10.1038/mtna.2011.4; published online Jan. 24, 2012; © 2012 American Society of Gene & Cell Therapy.

Communication pursuant to Rule 164(1) EPC for European Patent Application No. 16849742.8 dated Mar. 14, 2019; 13 pages.

Partial Search Report for 17869883.3 dated Apr. 24, 2020.

Extended EP Search Report for 17869883.3 dated Jul. 16, 2020. 16 pages.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Costa et al., "Toward RNAi therapy for the polyglutamine disease Machado-Joseph disease" Mol Ther (2013) 21: 1898-1908.

Crooke et al., "Basic Principles of Antisense Therapeutics" Antisense Research and Application (1998) Chapter 1:1-50.

New England Biolabs 1998/99 Catalog (cover page and pp. 121 and 284).

Reynolds et al., "Rational siRNA design for RNA interference" Nature Biotechnology (2004) 22(3):326-330.

(56) References Cited

OTHER PUBLICATIONS

Sanghvi et al., "Heterocyclic Base Modifications in Nucleic Acids and Their Applications in Antisense Oligonucleotides" International Search Report for PCT/US20/019272 dated Jul. 1, 2020.

* cited by examiner

COMPOSITIONS AND METHODS FOR MODULATING ATAXIN 3 EXPRESSION

SEQUENCE LISTING

The present application is being filed along with a Sequence Listing in electronic format. The Sequence Listing is provided as a file entitled BIOL0278WOSEQ_ST25.txt created Sep. 22, 2016, which is approximately 68 KB in size. The information in the electronic format of the sequence listing is incorporated herein by reference in its entirety.

BACKGROUND

1. Field

Disclosed herein are compositions and methods related to the fields of modified oligonucleotides, biochemistry, molecular biology, and medicine. Embodiments described herein relate to compounds, compositions, and methods for treating, preventing, or ameliorating neurodegenerative diseases, including spinocerebellar ataxia type 3 (SCA3) by modulating the splicing of Ataxin 3 (ATXN3) pre-mRNA in a cell and/or in an animal.

2. Description

Spinocerebellar ataxia type 3 (SCA3), also known as Machado-Joseph disease (MJD), is caused by a mutation in the ATXN3 gene and is characterized by progressive cerebellar ataxia and variable findings including a dystonic-rigid syndrome, a parkinsonian syndrome, or a combined syndrome of dystonia and peripheral neuropathy. SCA3 is inherited in an autosomal dominant manner. Offspring of affected individuals have a 50% chance of inheriting the mutation. The diagnosis of SCA3 rests on the use of molecular genetic testing to detect an abnormal CAG trinucleotide repeat expansion in ATXN3. Affected individuals have alleles with 52 to 86 CAG trinucleotide repeats. Such testing detects 100% of affected individuals. Expanded CAG repeats in the ATXN3 gene are translated into expanded polyglutamine repeats (polyQ) in the ataxin-3 protein and this toxin Ataxin 3 protein is associated with aggregates. The polyglutamine expanded ataxin-3 protein in these aggregates is ubiquinated and the aggregates contain other proteins, including heat shock proteins and transcription factors. Aggregates are frequently observed in the brain tissue of SCA3 patients. Management of SCA3 is supportive as no medication slows the course of disease; restless legs syndrome and extrapyramidal syndromes resembling parkinsonism may respond to levodopa or dopamine agonists; spasticity, drooling, and sleep problems respond variably to lioresal, atropine-like drugs, and hypnotic agents; botulinum toxin has been used for dystonia and spasticity; daytime fatigue may respond to psychostimulants such as modafinil; accompanying depression should be treated.

SUMMARY

Provided herein are compositions and methods for modulating splicing of ATXN3 pre-mRNA in cells, tissues, and animals. Also provided herein are methods for modulating the expression product of an Ataxin 3 mRNA in cells, tissues, and animals.

In certain embodiments, modulation can occur in a cell or tissue. In certain embodiments, the cell or tissue is in an animal. In certain embodiments, the animal is human. In certain embodiments, splicing of ATXN3 pre-mRNA is modulated. In certain embodiments, the expression product of an Ataxin 3 mRNA is modulated. In certain embodiments, partial or total exclusion of Ataxin 3 exon 9 is promoted. In certain embodiments, partial or total exclusion of Ataxin 3 exon 10 is promoted. In certain embodiments, expression of the toxic Ataxin 3 protein containing an expanded polyglutamine repeat is reduced. In certain embodiments, compounds and methods described herein remove exon 10 containing the CAG repeat from ATXN3 resulting in expression of a truncated ataxin-3 protein lacking the expanded polyglutamine repeat. The truncated ataxin-3 protein (termed A C-terminus) consists of 291 amino acids and has a predicated mass of 24 kDa, and lacks the polyQ repeat and ubiquitin interactive motif 3 (UIM3). Such reduction and modulation can occur in a time-dependent manner or in a dose-dependent manner.

Several embodiments are drawn to methods of reducing one or more symptoms or pathological hallmarks of an Ataxin 3-associated disorder. In certain embodiments, the symptom is ataxia, spastic gait, enhanced reflex responses, peripheral neuromuscular involvement (muscle twitching, weakness, atrophy, and abnormal sensations such as numbness, tingling, cramps, and pain in the hands and feet), double vision or blurred vision, loss of ability to distinguish color and/or contrast, inability to control eye movements, and Parkinson's disease-like symptoms, such as slowness of movement, rigidity or stiffness of the limbs and trunk, and tremor or trembling in the hands. In certain embodiments, the pathological hallmark is presence of aggregates. In certain embodiments, the Ataxin 3-associated disorder is spinocerebellar ataxia type 3 (SCA3). In certain embodiments, the methods comprise administering a modified oligonucleotide to the subject, wherein the modified oligonucleotide reduces expression of the toxic Ataxin 3 protein containing an expanded polyglutatime repeat in the central nervous system of the subject. In certain embodiments, one or more symptoms or pathological hallmarks of SCA3 is ameliorated, prevented, or delayed (progression slowed).

In certain embodiments, methods of treatment include administering an Ataxin 3 modified oligonucleotide to an individual in need thereof. In certain embodiments, each nucleoside of the Ataxin 3 modified oligonucleotide comprises a modified sugar. In certain embodiments, the modified sugar comprises a 2'-O-methoxyethyl (2'-MOE) group. In certain embodiments, the modified sugar does not comprise a 2'-O-methyl group (2'-OMe).

In certain embodiments, the modified oligonucleotide is complementary to exon 9, exon 10, the junction between exon 9 and a flanking intron of human Ataxin 3 pre-mRNA, or the junction between exon 10 and a flanking intron of Ataxin 3 pre-mRNA. In certain embodiments, the modified oligonucleotides exclude (i.e., skip) exon 9 from Ataxin 3 mRNA. In certain embodiments, the modified oligonucleotides exclude (i.e., skip) exon 10 from Ataxin 3 mRNA. In certain embodiments, excluding (i.e., skipping) exon 9 and/or 10 results in reduced expression of the toxic Ataxin 3 protein containing an expanded polyglutamine repeat.

The present disclosure provides the following non-limiting numbered embodiments:

Embodiment 1

An oligomeric compound comprising a modified oligonucleotide consisting of 15-25 linked nucleosides, wherein the oligonucleotide has a nucleobase sequence comprising at least 15, 16, 17, or 18 contiguous nucleobases of any one of SEQ ID NO: 4-11, wherein each nucleoside of the modified oligonucleotide comprises a 2'-O-methoxyethyl group.

Embodiment 2

The oligomeric compound of embodiment 1, wherein modified oligonucleotide consists of 18-22 linked nucleosides.

Embodiment 3

The oligomeric compound of any of embodiments 1-2, wherein the modified oligonucleotide has a nucleobase sequence comprising at least 19 or 20 contiguous nucleobases of SEQ ID NO: 4-10.

Embodiment 4

The oligomeric compound of any of embodiments 1-3, wherein the modified oligonucleotide has a nucleobase sequence comprising at least 21 contiguous nucleobases of SEQ ID NO: 4, 6, or 7.

Embodiment 5

The oligomeric compound of any of embodiments 1-3, wherein the modified oligonucleotide has a nucleobase sequence comprising at least 22 contiguous nucleobases of SEQ ID NO: 4 or 6.

Embodiment 6

The oligomeric compound of any embodiments 1-5, wherein the modified oligonucleotide is single-stranded.

Embodiment 7

The oligomeric compound of any of embodiments 1-6, wherein at least one internucleoside linkage of the modified oligonucleotide is a modified internucleoside linkage.

Embodiment 8

The oligomeric compound of embodiment 7, wherein each internucleoside linkage of the modified oligonucleotide is a modified internucleoside linkage.

Embodiment 9

The oligomeric compound of embodiments 7 or 8, wherein the modified internucleoside linkage is a phosphorothioate internucleoside linkage.

Embodiment 10

The oligomeric compound of any of embodiments 1-9, wherein at least one nucleobase of the modified oligonucleotide is a modified nucleobase.

Embodiment 11

The oligomeric compound of embodiment 10, wherein the modified nucleobase is a 5-methylcytosine.

Embodiment 12

The oligomeric compound of any of embodiments 1-11, wherein each nucleobase of each nucleoside of the modified oligonucleotide is either an unmodified nucleobase or is a 5-methylcytosine.

Embodiment 13

An oligomeric compound comprising a modified oligonucleotide consisting of 22 linked nucleosides and having the nucleobase sequence of SEQ ID NO: 4 or 6, wherein each nucleoside of the modified oligonucleotide comprises a modified sugar moiety that is other than a 2'-O-methyl modified sugar.

Embodiment 14

An oligomeric compound comprising a modified oligonucleotide consisting of 21 linked nucleosides and having the nucleobase sequence of SEQ ID NO: 7, wherein each nucleoside of the modified oligonucleotide is a modified sugar that is not a 2'-O-methyl modified sugar.

Embodiment 15

An oligomeric compound comprising a modified oligonucleotide consisting of 20 linked nucleosides and having the nucleobase sequence of any of SEQ ID NO: 5 or 8-10, wherein each nucleoside of the modified oligonucleotide is a modified sugar that is not a 2'-O-methyl modified sugar.

Embodiment 16

An oligomeric compound comprising a modified oligonucleotide consisting of 18 linked nucleosides and having the nucleobase sequence of SEQ ID NO: 11, wherein each nucleoside of the modified oligonucleotide is a modified sugar that is not a 2'-O-methyl modified sugar.

Embodiment 17

A modified oligonucleotide consisting of 22 linked nucleosides and having the nucleobase sequence of SEQ ID NO: 4 or 6, wherein each nucleoside of the modified oligonucleotide comprises a modified sugar moiety that is other than a 2'-O-methyl modified sugar.

Embodiment 18

A modified oligonucleotide consisting of 21 linked nucleosides and having the nucleobase sequence of SEQ ID NO: 7, wherein each nucleoside of the modified oligonucleotide is a modified sugar that is not a 2'-O-methyl modified sugar.

Embodiment 19

A modified oligonucleotide consisting of 20 linked nucleosides and having the nucleobase sequence of any of SEQ ID NO: 5 or 8-10, wherein each nucleoside of the modified oligonucleotide is a modified sugar that is not a 2'-O-methyl modified sugar.

Embodiment 20

A modified oligonucleotide consisting of 18 linked nucleosides and having the nucleobase sequence of SEQ ID NO: 11, wherein each nucleoside of the modified oligonucleotide is a modified sugar that is not a 2'-O-methyl modified sugar.

Embodiment 21

The oligomeric compound of any of embodiments 13-16 or the modified oligonucleotide of any of embodiments 17-20, wherein each modified sugar is a bicyclic sugar.

Embodiment 22

The oligomeric compound or the modified oligonucleotide of embodiment 21, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently H, C$_1$-C$_6$ alkyl, and C$_1$-C$_6$ alkoxy.

Embodiment 23

The oligomeric compound or the modified oligonucleotide of embodiment 22, wherein the chemical bridge is 4'-CH(R)—O-2' and wherein R is methyl.

Embodiment 24

The oligomeric compound or the modified oligonucleotide of embodiment 22, wherein the chemical bridge is 4'-CH(R)—O-2' and wherein R is H.

Embodiment 25

The oligomeric compound or the modified oligonucleotide of embodiment 22, wherein the chemical bridge is 4'-CH(R)—O-2' and wherein R is —CH$_2$—O—CH$_3$.

Embodiment 26

The oligomeric compound or the modified oligonucleotide of any of embodiments 13-20, wherein the modified sugar comprises a 2'-O-methoxyethyl group.

Embodiment 27

The oligomeric compound of any of embodiments 13-16 or the modified oligonucleotide of any of embodiments 17-20, wherein each modified sugar is a morpholino.

Embodiment 28

The oligomeric compound of any of embodiments 13-16 or the modified oligonucleotide of any of embodiments 17-20, wherein the modified oligonucleotide is single-stranded.

Embodiment 29

The oligomeric compound of any of embodiments 13-16 or the modified oligonucleotide of any of embodiments 17-20, wherein at least one internucleoside linkage of the modified oligonucleotide is a modified internucleoside linkage.

Embodiment 30

The oligomeric compound or the modified oligonucleotide of embodiment 29, wherein each internucleoside linkage of the modified oligonucleotide is a modified internucleoside linkage.

Embodiment 31

The oligomeric compound or the modified oligonucleotide of embodiments 29 or 30, wherein the modified internucleoside linkage is a phosphorothioate internucleoside linkage.

Embodiment 32

The oligomeric compound of any of embodiments 13-16 or the modified oligonucleotide of any of embodiments 17-20, wherein at least one nucleobase of the modified oligonucleotide is a modified nucleobase.

Embodiment 33

The oligomeric compound of any of embodiments 13-16 or the modified oligonucleotide of any of embodiments 17-20, wherein each nucleobase of each nucleoside of the modified oligonucleotide is either an unmodified nucleobase or is 5-methylcytosine.

Embodiment 34

The oligomeric compound or the modified oligonucleotide of embodiment 32, wherein the modified nucleobase is a 5-methylcytosine.

Embodiment 35

A composition comprising the oligomeric compound or the modified oligonucleotide according to any preceding embodiment or a salt thereof and a pharmaceutically acceptable carrier or diluent.

Embodiment 36

An oligomeric compound, a modified oligonucleotide, or a composition according to any preceding embodiment for use in treating, preventing, or ameliorating at least one symptom of spinocerebellar ataxia type 3.

Embodiment 37

A method of modulating splicing of Ataxin-3 pre-mRNA in a cell comprising contacting a cell with an oligomeric compound wherein the oligomeric compound comprises a modified oligonucleotide consisting of 15-25 linked nucleosides and has a nucleobase sequence comprising at least 15, 16, 17, or 18 contiguous nucleobases of any one of SEQ ID NO: 4-11, wherein at least one nucleoside of the modified oligonucleotide comprises a sugar moiety that is other than a 2'-O-methyl modified sugar.

Embodiment 38

The method of embodiment 37, wherein the modified oligonucleotide comprises at least one nucleoside comprising a modified sugar moiety.

Embodiment 39

The method of embodiment 37, wherein each nucleoside of the modified oligonucleotide comprises a modified sugar moiety.

Embodiment 40

The method of embodiment 37 or 38, wherein at least one nucleoside of the modified oligonucleotide is a 2'-deoxynucleoside.

Embodiment 41

The method of any of embodiments 37-40, wherein the modified oligonucleotide comprises at least one nucleoside comprising a modified sugar moiety selected from among: 2'-MOE, morpholino, and a bicyclic nucleoside.

Embodiment 42

The method of any of embodiments 37-39 or 41 wherein the sugar modification of each nucleoside of the modified oligonucleotide are the same as one another.

Embodiment 43

The method of any of embodiments 37-42 wherein the cell is in vitro.

Embodiment 44

The method of any of embodiments 37-42 wherein the cell is in an animal.

Embodiment 45

An oligomeric compound for modulating splicing of Ataxin-3 pre-mRNA in a cell comprising contacting a cell with an oligomeric compound wherein the oligomeric compound comprises a modified oligonucleotide consisting of 15-25 linked nucleosides and has a nucleobase sequence comprising at least 15, 16, 17, or 18 contiguous nucleobases of any one of SEQ ID NO: 4-11, wherein at least one nucleoside of the modified oligonucleotide comprises a sugar moiety that is other than a 2'-O-methyl modified sugar.

Embodiment 46

The oligomeric compound of embodiment 45, wherein the modified oligonucleotide comprises at least one nucleoside comprising a modified sugar moiety.

Embodiment 47

The oligomeric compound of embodiment 45, wherein each nucleoside of the modified oligonucleotide comprises a modified sugar moiety.

Embodiment 48

The oligomeric compound of embodiment 45 or 46, wherein at least one nucleoside of the modified oligonucleotide is a 2'-deoxynucleoside.

Embodiment 49

The oligomeric compound of any of embodiments 45-48, wherein the modified oligonucleotide comprises at least one nucleoside comprising a modified sugar moiety selected from among: 2'-MOE, morpholino, and a bicyclic nucleoside.

Embodiment 50

The oligomeric compound of any of embodiments 45-47 or 49 wherein the sugar modification of each nucleoside of the modified oligonucleotide are the same as one another.

Embodiment 51

The oligomeric compound of any of embodiments 45-50 wherein the cell is in vitro.

Embodiment 52

The oligomeric compound of any of embodiments 45-50 wherein the cell is in an animal.

Embodiment 53

A method comprising administering to an animal having or at risk for developing SCA3 a therapeutically effective amount of an oligomeric compound according to any of embodiments 1-16 or a modified oligonucleotide according to any one of embodiments 17-20 or a composition according to embodiment 35; wherein the administering reduces the number and/or volume of aggregates in brain tissue.

Embodiment 54

The method of embodiment 53, wherein the brain tissue is any of brainstem, cerebellum, or cortex.

Embodiment 55

The oligomeric compound of any of embodiments 1-16, 21-34, 36, and 45-52, consisting of the modified oligonucleotide.

Figure 5:
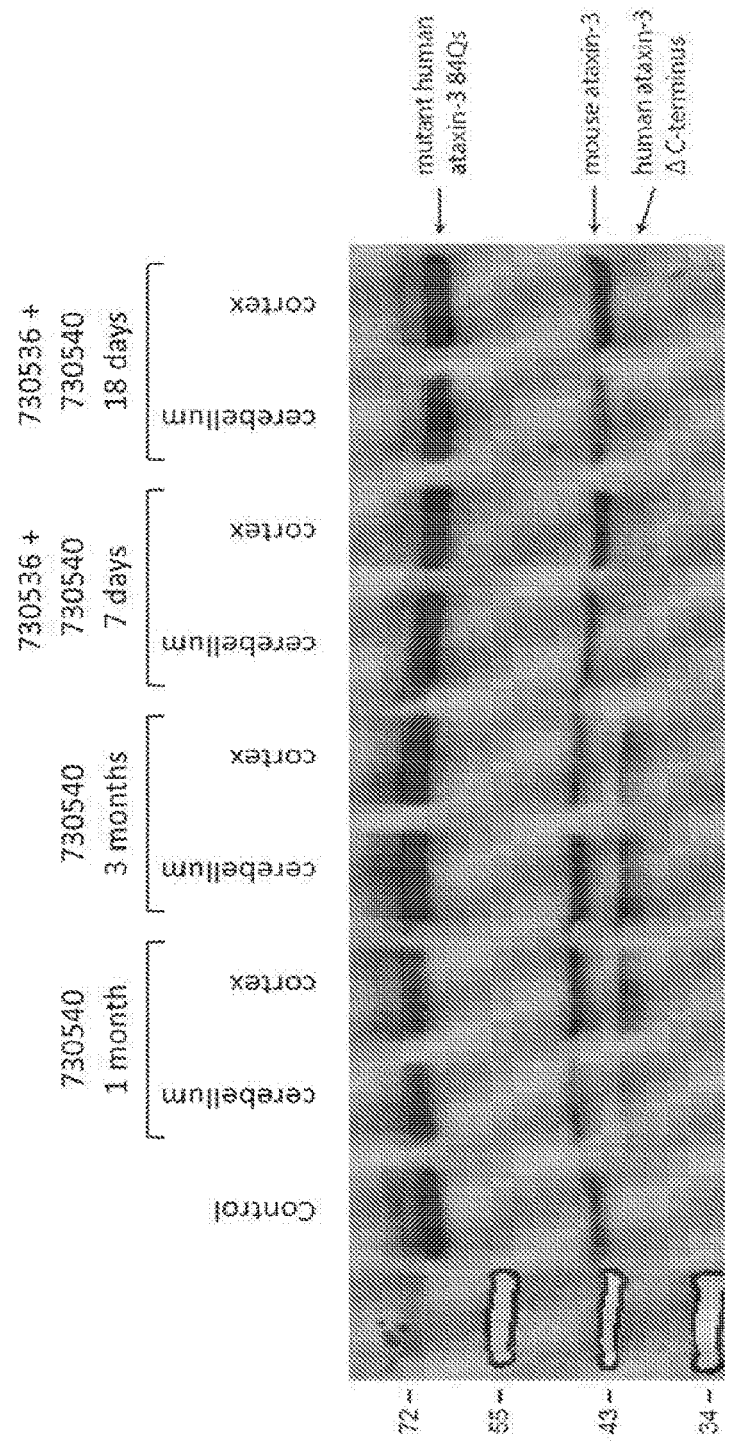

FIG. 5 shows a western blot for human and mouse ATXN3. The protein was isolated from MJD84.2/SCA3 mice treated with one or two 2'-MOE modified oligonucleotides targeting exon 9 and/or exon 10 of human ATXN3 or a control oligonucleotide.

Figure 6:
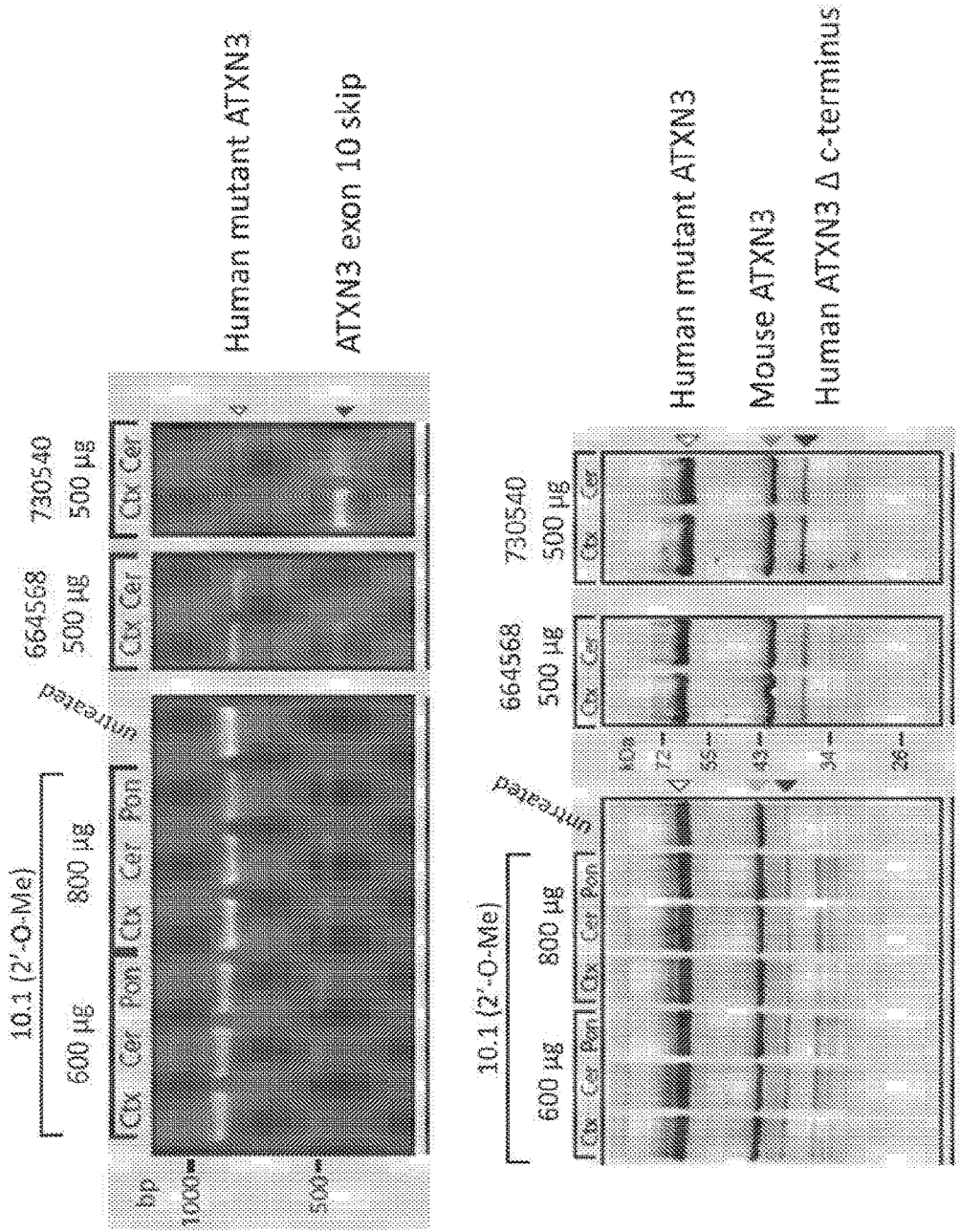

FIG. 6 shows a DNA gel following RT-PCR with human specific primers and a western blot. The RNA and protein was isolated from MJD84.2/SCA3 mice treated with a 2'-MOE modified oligonucleotide, a 2'-O-methyl modified oligonucleotide, or no treatment.

Figure 7:
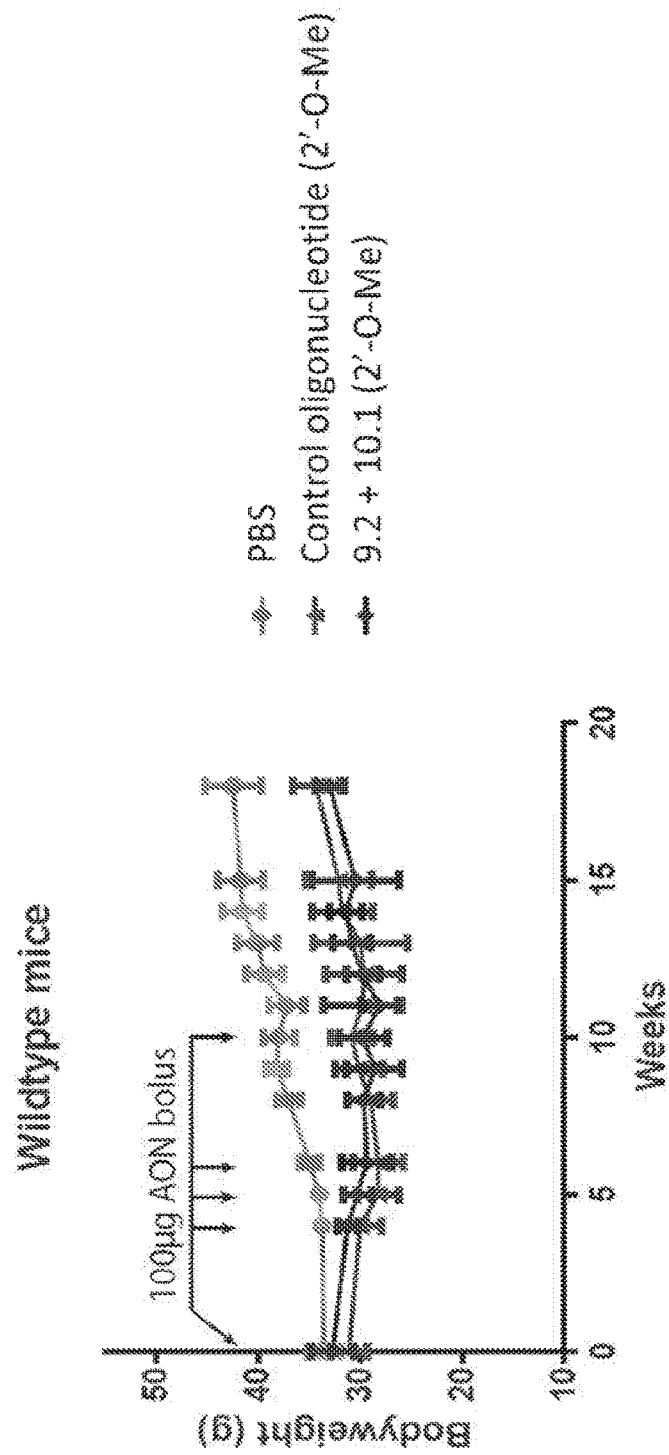

FIG. 7 shows the effect of 2'-O-methyl modified oligonucleotides (9.2+10.1) on body weight in wild type mice.

Figure 8:
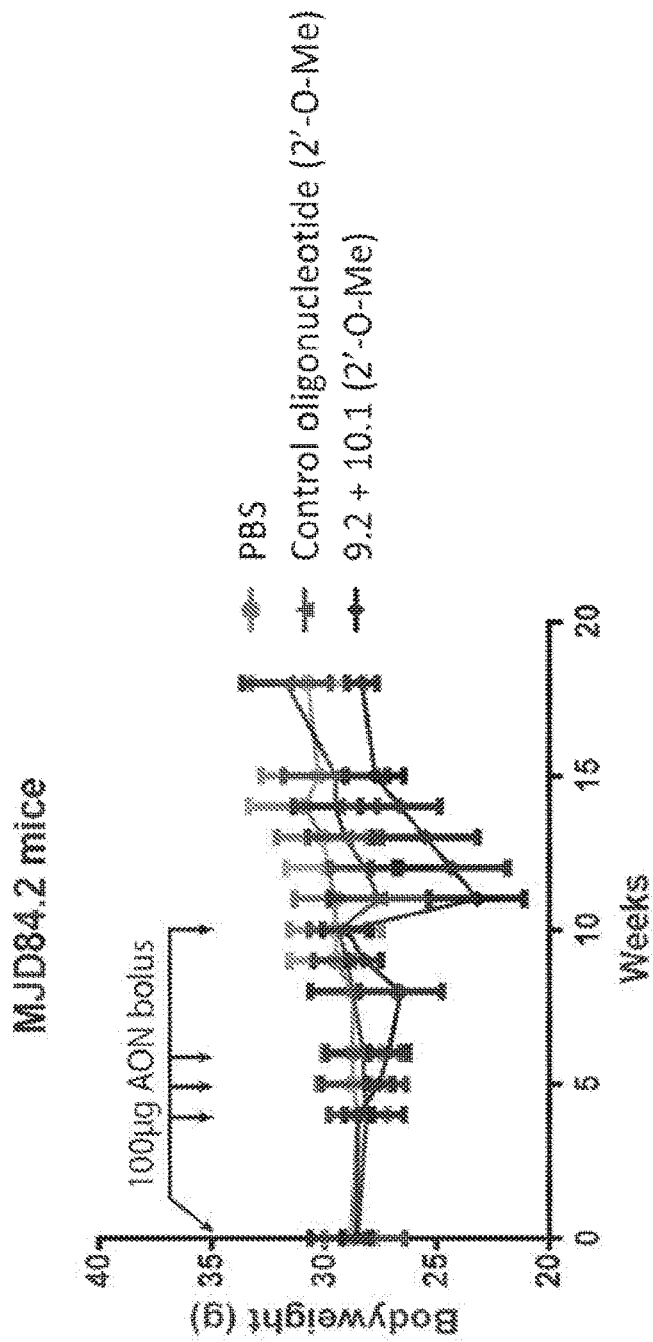

FIG. 8 shows the effect of 2'-O-methyl modified oligonucleotides (9.2+10.1) on body weight in MJD84.2/SCA3 mice.

Figure 9:
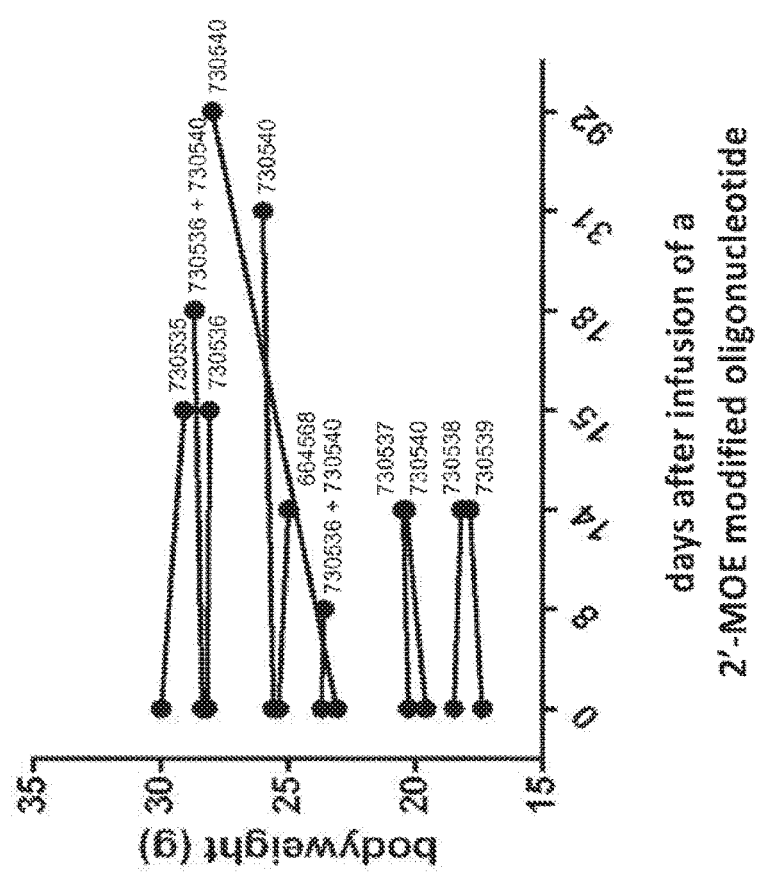

FIG. 9 shows the effect of 2'-MOE modified oligonucleotides (Compounds 664568, 730535, 730536, 730537, 730538, 730539, 730540, and 730536+730540) on body weight in wild type mice.

Figure 10:
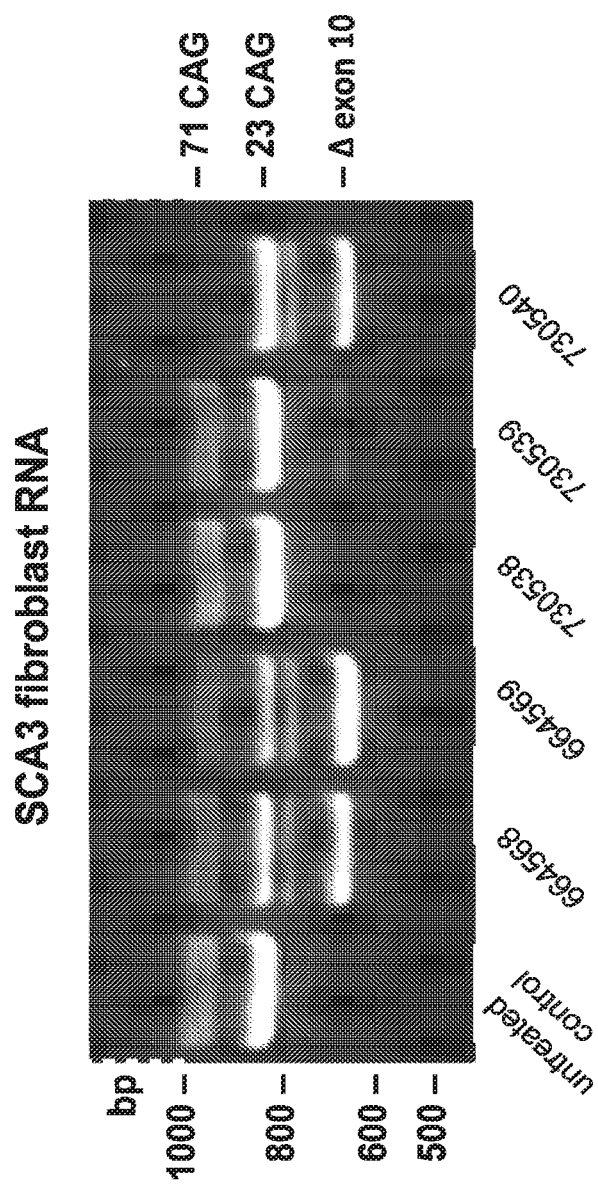

FIG. 10 shows ASO-mediated truncation of Ataxin-3 RNA lacking the CAG repeat was detected in SCA3 fibroblasts.

Figure 11:
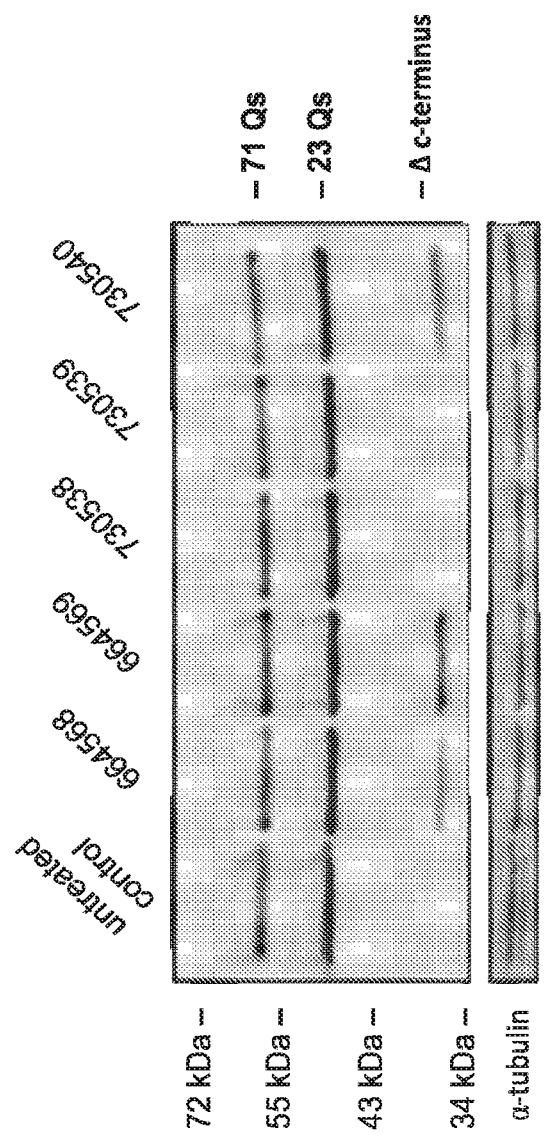

FIG. 11 shows ASO-mediated truncation of Ataxin-3 protein lacking the polyglutamine containing C-terminus was detected in SCA3 fibroblasts.

Figure 12:
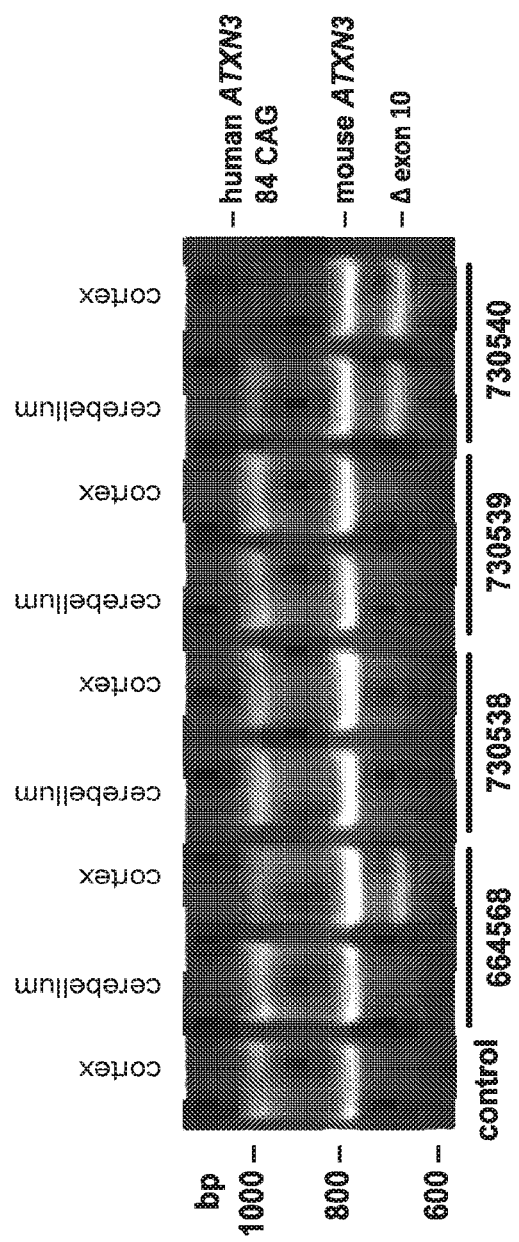

FIG. 12 provides RT-PCR results using primers flanking ATXN3 exon 10 showing the full length human ataxin-3 PCR product with 84 CAG repeats, the mouse ataxin-3 with 6 CAG repeats, and the truncated ataxin-3 lacking exon 10 after treatment with modified oligonucleotides.

Figure 13:
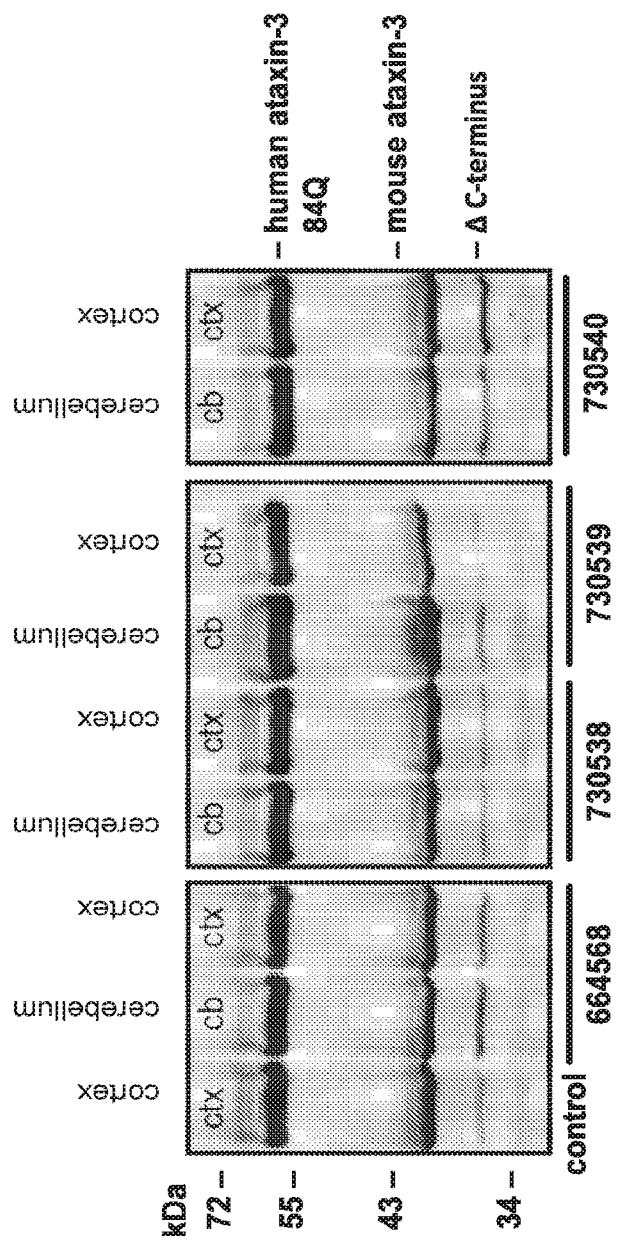

FIG. 13 provides Western blotting showing the full length human ataxin-3 protein with 84 polyglutamine repeats, the mouse ataxin-3 protein with 6 polyglutamine repeats, and the truncated ataxin-3 protein lacking the C-terminus (A C-terminus).

Figure 14:
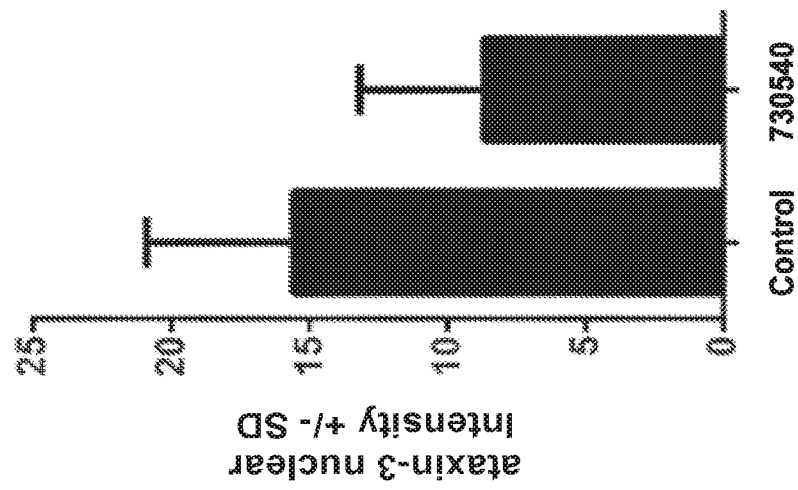

FIG. 14 provides a bar graph depicting quantification of staining intensity showing that transgenic mice treated with compound 730540 have decreased nuclear accumulation of ataxin-3 in cells of substantia nigra as compared to transgenic mice treated with a control compound.

Figure 15:
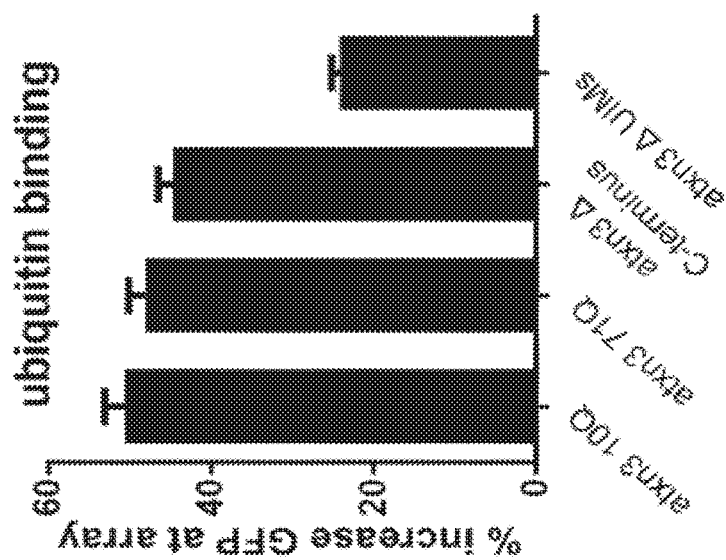

FIG. 15 provides a bar graph depicting quantification of percentage increase in GFP-tagged ataxin-3 at the array after co-transfection with RNF8 construct revealing that ataxin-3 Δ C-terminus is capable of binding ubiquitin chains.

DETAILED DESCRIPTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose.

Where permitted, all patents, applications, published applications and other publications and other data referred to throughout in the disclosure are incorporated by reference herein in their entirety.

Compounds of the invention include variations of the disclosed compounds in which one or more hydrogen, carbon, nitrogen, oxygen, or sulfur atoms is replaced with a stable isotope of the same element. Unless otherwise indicated, the following terms have the following meanings:

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

As used herein, "Antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the antisense compound.

As used herein, "Antisense compound" means a compound comprising an antisense oligonucleotide and optionally one or more additional features, such as a conjugate group or terminal group.

"Antisense oligonucleotide" (ASO) means an oligonucleotide that (1) has a nucleobase sequence that is at least partially complementary to a target nucleic acid and that (2) is capable of producing an antisense activity in a cell or animal.

As used herein, "Ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "Ataxin 3 associated disorder" means a disorder associated with Ataxin-3. Spinocerebellar ataxia type 3 (SCA3) is an Ataxin-3 associated disorder. "An animal having or at risk for developing SCA3" is an animal having been diagnosed with SCA3 or an animal genetically predisposed to develop SCA3. Such diagnosis may be accomplished by, for example, clinical evaluation and genetic testing.

As used herein, "Bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression of activity in an untreated or control sample and does not necessarily indicate a total elimination of expression or activity.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages.

As used herein, "Phosphorothioate linkage" means a modified phosphate linkage in which one of the non-bridging oxygen atoms is replaced with a sulfur atom. A phosphorothioate internucleoside linkage is a modified internucleoside linkage.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar" or "non-bicyclic modified sugar moiety" means a modified sugar moiety that comprises a modification, such as a substitutent, that does not form a bridge between two atoms of the sugar to form a second ring.

As used herein, "linked nucleosides" are nucleosides that are connected in a continuous sequence (i.e. no additional nucleosides are present between those that are linked).

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "MOE" means methoxyethyl. "2'-MOE" means a —OCH$_2$CH$_2$OCH$_3$ group at the 2' position of a furanosyl ring.

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a modified nucleobase is a group of atoms (other than an unmodified nucleobase) capable of pairing with at least one unmodified nucleobase. A universal base is a nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "reduces the number and/or volume of aggregates in brain tissue" means a reduction in the number and/or volume of aggregates in brain tissue in an animal diagnosed with having expanded polyglutamine repeats in the ataxin-3 protein and treated with an oligomeric compound complementary to Ataxin-3 as compared to an animal without expanded polyglutamine repeats in the ataxin-3 protein and/or not treated with an oligomeric compound complementary to Ataxin-3. Quantification may be accomplished by any method including measuring the intensity of aggregates such as described in Example 8.

As used herein, the term "single-stranded" in reference to an oligonucleotide means such a oligonucleotide (including an oligonucleotide of an oligomeric compound) that is not paired with a second oligonucleotide or oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex at which point it is no longer single-stranded.

As used herein, "standard cell assay" means the assay described in Example 1 and reasonable variations thereof.

As used herein, "standard in vivo experiment" means the procedure described in Example 2 and reasonable variations thereof.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid" means a naturally occurring identified nucleic acid. In certain embodiments, target nucleic acids are nucleic acids that an antisense compound is designed to affect.

As used herein, "target region" means a portion of a target nucleic acid to which an antisense compound is designed to hybridize.

As used herein, "terminal group" means a chemical group or group of atoms that is covalently linked to a terminus of an oligonucleotide.

As used herein, "therapeutically effective amount" means an amount of pharmaceutical agent that provides a therapeutic benefit to an individual.

I. Certain Oligonucleotides

In certain embodiments, the invention provides oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C—(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

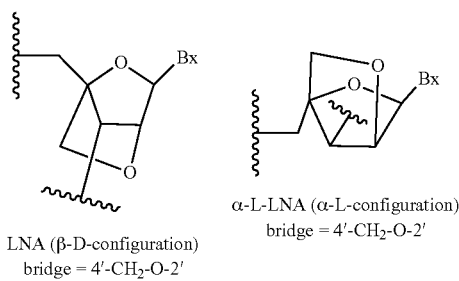

LNA (β-D-configuration)
bridge = 4'-CH₂-O-2'

α-L-LNA (α-L-configuration)
bridge = 4'-CH₂-O-2'

α-L-methyleneoxy (4'-CH₂—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. Bioorg. & Med. Chem. 2002, 10, 841-854), fluoro HNA:

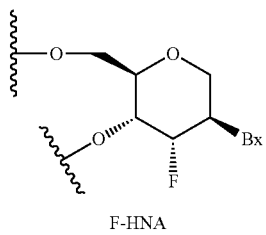

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

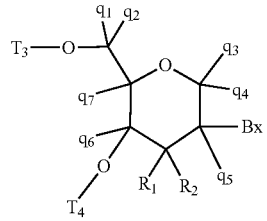

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

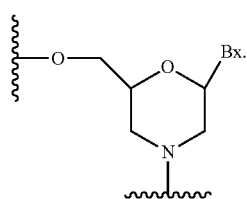

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, a modified nucleobase is 5-methylcytosine. In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65).

Further neutral internucleoside linkages include nonionic linkages comprising mixed N, O, S and $CH_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification. In certain embodiments, uniformly modified oligonucleotides comprise nucleosides that are each 2'MOE modified. In certain embodiments, uniformly modified oligonucleotides comprise nucleosides that are each morpholino.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines. In certain embodiments, all of the nucleobases of an oligonucleotide are naturally occurring nucleobases or 5-methylcytosines. In certain such embodiments, all of the cytosines are 5-methylcytosines.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the terminal internucleoside linkages are modified.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides

E. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide uniform motif may be modified or unmodified and may or may not follow the sugar modification pattern. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range.

In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a uniform sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Compounds

In certain embodiments, the present invention provides antisense compounds, which comprise or consist of an oligomeric compound comprising an antisense oligonucleotide, having a nucleobase sequence complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligomeric compounds of antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved.

B. Ataxin 3

In certain embodiments, antisense compounds comprise or consist of an oligonucleotide comprising a region that is complementary to a target nucleic acid, wherein the target nucleic acid is Ataxin 3. In certain embodiments, Ataxin 3 nucleic acid has the sequence set forth in the complement of GENBANK accession number NT 026437.12 truncated from nucleotides 73524000 to 73574000 incorporated herein as SEQ ID NO: 1.

In certain embodiments, contacting a cell with an antisense compound complementary to SEQ ID NO: 1 reduces expression of toxic Ataxin 3 protein containing a polyglutamine repeat. In certain embodiments, contacting a cell with an antisense compound complementary to SEQ ID NO: 1 ameliorates one or more symptoms or pathological hallmarks of spinocerebellar ataxia type 3 (SCA3). In certain embodiments, the pathological hallmark is presence of aggregates. In certain embodiments, contacting a cell with an oligomeric compound complementary to SEQ ID NO: 1 reduces the number and/or volume of aggregates in brain tissue.

C. Certain Target Nucleic Acids in Certain Tissues

In certain embodiments, antisense compounds comprise or consist of an oligonucleotide comprising a region that is complementary to a target nucleic acid, wherein the target nucleic acid is expressed in CNS tissue, including brain tissue, such as cortex, cerebellum, pons, brainstem, and cortex.

IV. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

V. Certain Routes of Administration

Administration includes parenteral routes of administration, such as intraperitoneal, intravenous, and subcutaneous, as well as central routes of administration such as intracerebroventricular or intrathecal. Following a period of treatment with antisense oligonucleotides, RNA or protein is isolated from CNS tissue or CSF and changes in Ataxin 3 nucleic acid or protein expression are measured.

VI. Certain Combination Treatments

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein pharmaceutical agents that ameliorate symptoms of SCA3 including levodopa or dopamine agonists to address restless legs syndrome and extrapyramidal syndromes resembling parkinsonism; lioresal, atropine-like drugs, and hypnotic agents to address spasticity, drooling, and sleep problems; botulinum toxin for dystonia and spasticity; and psychostimulants such as modafinil for daytime fatigue.

In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds are intended to include corresponding salts.

Examples

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: 2'MOE Modified Oligonucleotide Modulation of Human ATXN3 Transcript Splicing In Vitro Modified oligonucleotides complementary to exon 9, exon 10, or the junction between exon 9 or exon 10 and a flanking intron of human Ataxin-3 (ATXN3) pre-mRNA were synthesized and tested for their ability to modulate splicing of ATXN3. The oligonucleotides target the complement of GENBANK accession number NT_026437.12 truncated from nucleotides 73524000 to 73574000 (SEQ ID NO: 1). The oligonucleotides listed in the table below, except Compound No. 730540, are 100% complementary to SEQ ID NO: 1. Compound No. 730540 has one mismatch at position 36,647 of SEQ ID NO: 1. The nucleosides of these modified oligonucleotides all had 2'-MOE sugar moieties and all internucleoside linkages were phosphorothioate linkages (uniform 2'-MOE/uniform PS). All cytosine bases were 5-methylcytosine, and the nucleobase sequences are listed in the table below. The start and stop sites associated with each oligonucleotide are the 5'- and 3'-positions, respectively, of the portion of SEQ ID NO: 1 that is complementary to the oligonucleotide.

Figure 1:
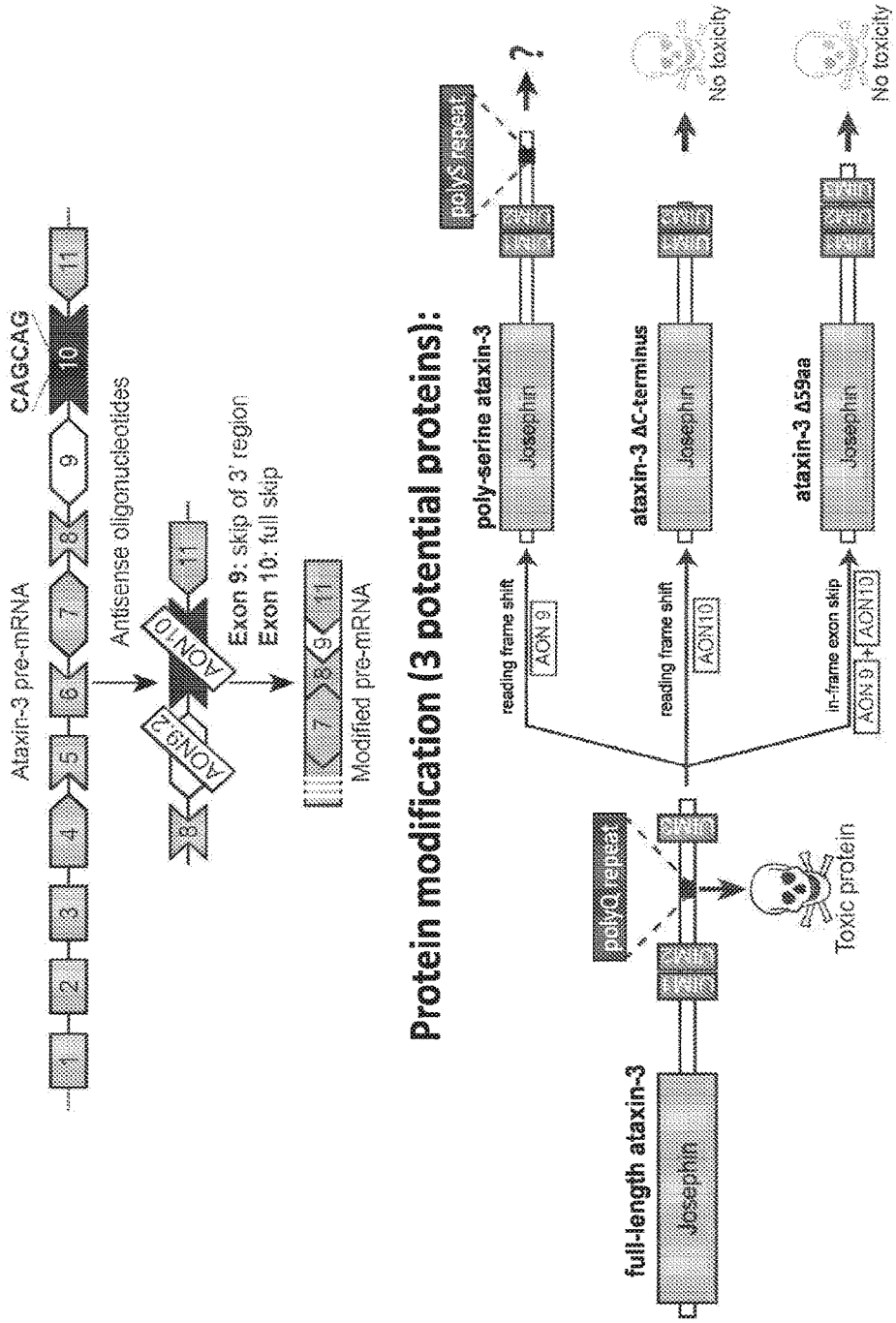
FIG. 1 depicts the exon skipping strategy for excluding the toxic CAG repeat in exon 10 of ATXN3.
Figure 2:
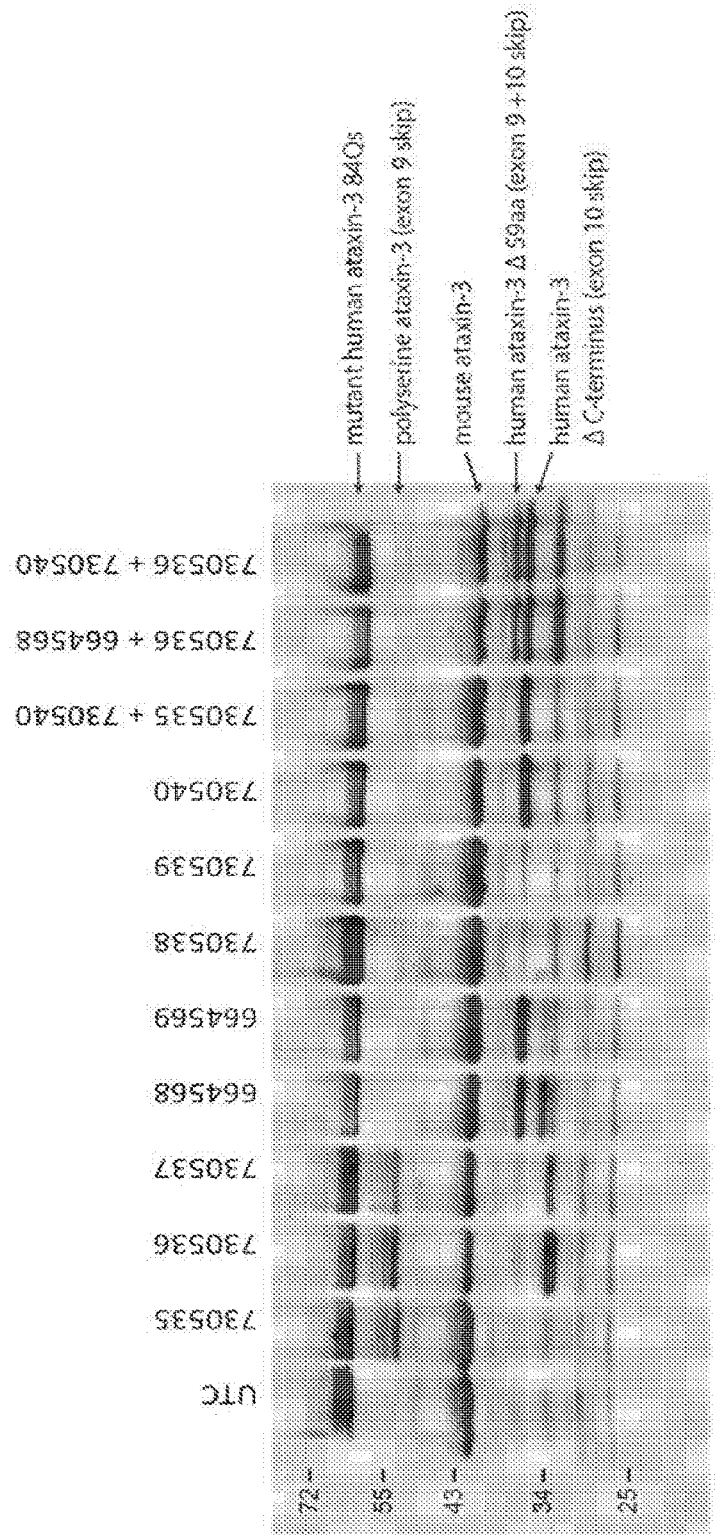
FIG. 2 shows a western blot for human and mouse ATXN3. The protein was isolated from MJD84.2 mouse derived myoblasts that express human mutant ATXN3 following transfection with 2'-MOE modified oligonucleotides targeting exon 9 or exon 10 of human ATXN3.

To test the ability of the oligonucleotides to exclude (i.e., skip) exon 9 and/or exon 10 from ATXN3 mRNA, myoblasts isolated from the MJD84.2 mouse, which carries a YAC containing the full human ATXN3 gene containing 84 CAG repeats in exon 10 were transfected with 200 nM of one or two oligonucleotides listed in the table below using Lipofectamine 2000. Untransfected control cells (UTC) did not receive oligonucleotide treatment. After 48 hours, total protein was collected from the cells and analyzed by western blot using mouse SCA3-1H9 antibody (Millipore, Billerica, USA), which is reactive to human and mouse ATXN3. Exclusion of exon 9, exon 10, or both exons 9 and 10 from the mRNA results in one of three modified ATXN3 proteins. Exclusion of exon 9 or exon 10 results in a reading frame shift that causes either the CAG repeat in exon 10 to be translated to poly-serine or introduction of a premature stop codon and a truncated C-terminus, respectively. Exclusion of both exon 9 and exon 10 results in a deletion of 59 amino acids (FIG. 1). These three protein modifications were identified in the western blot shown in FIG. 2. The results in FIG. 2 indicate that the oligonucleotides targeting exon 9 caused exon 9 exclusion and translation of the poly-serine modified ATXN3 protein by this method, some of the oligonucleotides targeting exon 10 caused exon 10 exclusion and translation of the truncated ATXN3 protein that was detectable by this method, and some combinations of oligonucleotides targeting exon 9 and exon 10 caused exclusion of both exons 9 and 10 and translation of the modified ATXN3 missing 59 amino acids.

TABLE 1

2'MOE modified oligonucleotides for modulating ATXN3 expression

| Compound No. | Sequence (5' to 3') | Start site | Stop site | SEQ ID NO. |
|---|---|---|---|---|
| 664568 | GCTGTTGCTGCTTTTGCTGCTG | 36605 | 36626 | 4 |
| 664569 | CTGTTGCTGCTTTTGCTGCT | 36606 | 36625 | 5 |
| 730535 | GAGATATGTTTCTGGAACTACC | 26595 | 26616 | 6 |
| 730536 | GCTTCTCGTCTCTTCCGAAGC | 26660 | 26680 | 7 |
| 730537 | CCGAAGCTCTTCTGAAGTAA | 26647 | 26666 | 8 |
| 730538 | GAACTCTGTCCTGATAGGTC | 36650 | 36669 | 9 |
| 730539 | CTAGATCACTCCCAAGTGCT | 36703 | 36722 | 10 |
| 730540 | ATAGGTCCCGCTGCTGCT | 36639 | 36656 | 11 |

Figure 3:
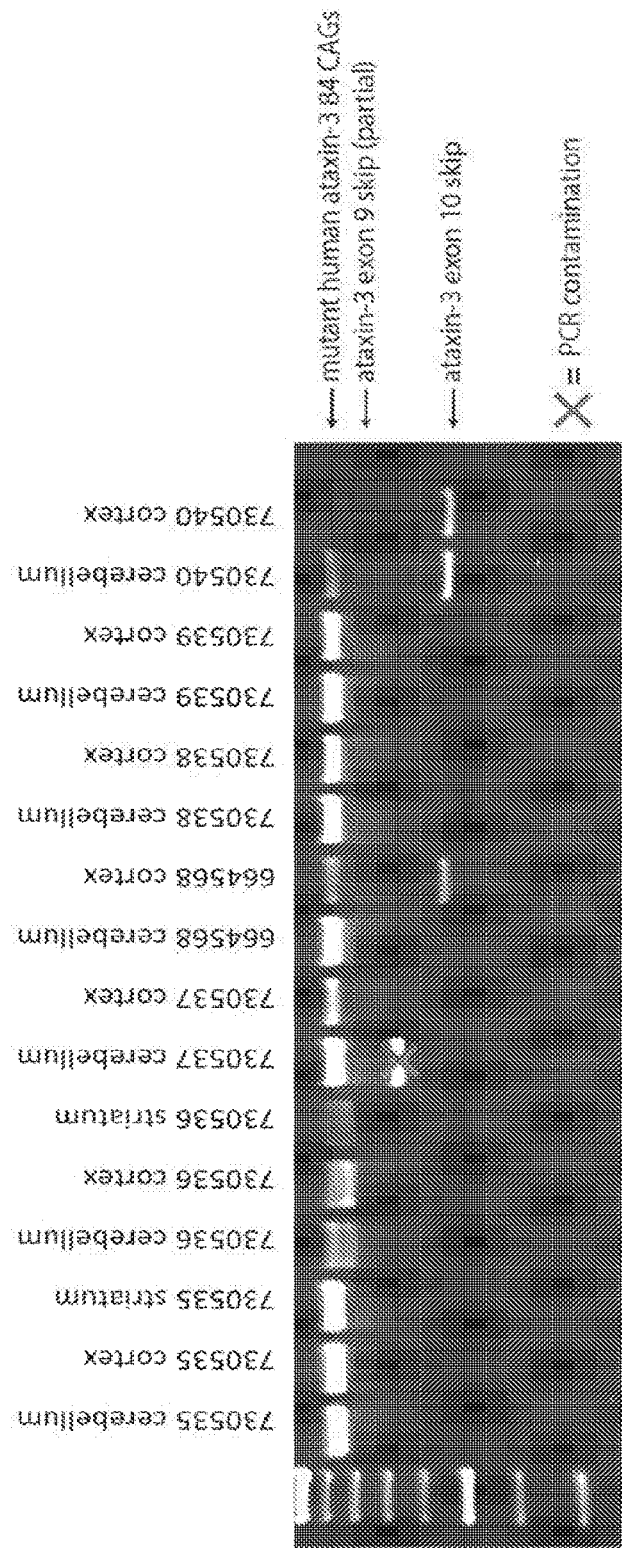
FIG. 3 shows a DNA gel. The DNA was generated by RT-PCR of RNA isolated from MJD84.2/SCA3 mice treated with a 2'-MOE modified oligonucleotide targeting exon 9 or exon 10 of human ATXN3.
Figure 4:
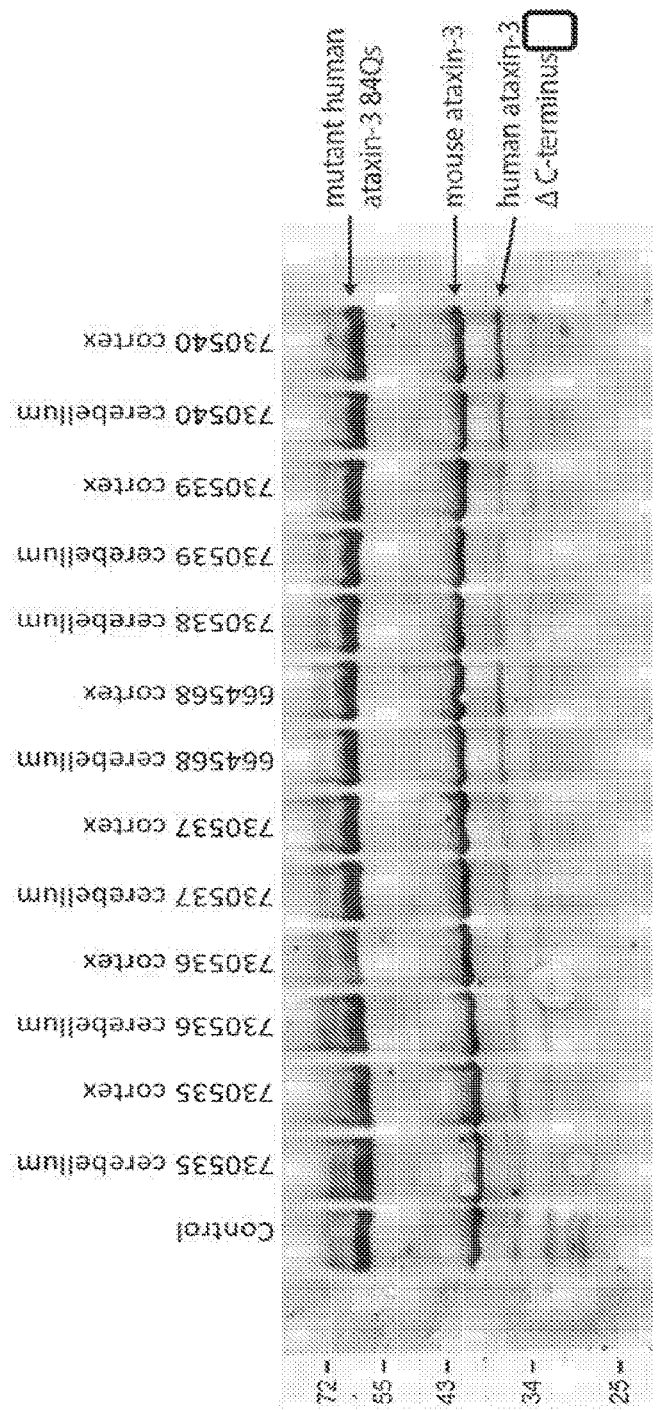
FIG. 4 shows a western blot for human and mouse ATXN3. The protein was isolated from MJD84.2/SCA3 mice treated with a 2'-MOE modified oligonucleotide targeting exon 9 or exon 10 of human ATXN3 or a control oligonucleotide.

Example 2: 2'MOE Modified Oligonucleotide Modulation of Human ATXN3 Transcript Splicing In Vivo The oligonucleotides described in Example 1 were tested for their effects on splicing of human ATXN3 RNA in vivo in MJD84.2/SCA3 transgenic mice available through Jackson Laboratory (Cemal, et al. (2002). The MJD84.2/SCA3 transgenic mice carrying pathological alleles of the MJD1 locus exhibit a mild and slowly progressive cerebellar deficit. (Hum Mol Genet 11, 1075-1094) Groups of MJD84.2/SCA3 mice aged 2.5 months or 7 months received a single 500 µg intracerebroventricular injection of an oligonucleotide described in Example 1 or a control oligonucleotide that does not target ATXN3. Two weeks after the single ICV injection, the mice were euthanized and RNA and protein was isolated from the cortex and cerebellum. RT-PCR was performed to selectively amplify the human ATXN3 transcripts using primers: Forward primer (exon 8) CCATAAAACAGACCTGGAACG (incorporated herein as SEQ ID NO: 2) and human ATXN3 specific reverse primer (3'UTR) CGCATTGTTCCACTTTCCCA (incorporated herein as SEQ ID NO: 3). Western blot was also performed as described in Example 1. The RT-PCR results in FIG. 3 indicate that oligonucleotides targeting exon 9 caused exon 9 skipping in vivo that was detectable by this method, and oligonucleotides targeting exon 10 caused exon 10 skipping in vivo that was detectable by this method. The western blot results in FIG. 4 indicate that oligonucleotides targeting exon 10 caused production of a truncated ATXN3 protein that was detectable by this method.

Example 3: 2'MOE Modified Oligonucleotide Modulation of Human ATXN3 Transcript Splicing In Vivo Compound Numbers 730540 and 730536 in combination with 730540 (described in Example 1) were tested for their effects on splicing of human ATXN3 RNA in vivo. Groups consisting of one or two MJD84.2/SCA3 transgenic mice each aged either 2, 3, or 8 months received a single injection containing 500 µg intracerebroventricular injection of one oligonucleotide described in Example 1, a control 2'-OMe modified oligonucleotide that does not target ATXN3, or a single injection containing 250 µg of each of two oligonucleotides, under anesthesia. Seven days, eighteen days, one month, three months, or four months after the single ICV injection, the mice were euthanized and protein was isolated from the cortex and cerebellum. The treatment regimen for each group of mice is shown in the table below. Western blot was performed as described in Example 1. The results shown in FIG. 5 indicate that Compound No. 730540 targeting exon 10 caused production of truncated ATXN3 protein that was detectable by this method, in both the cortex and cerebellum, at certain time points.

TABLE 2

Treatment groups

| Treatment group | Compound No. | Dosage (µg) | Treatment duration |
|---|---|---|---|
| 1 | n/a, 2'-O—Me Control | 500 | 4 months |
| 2 | 730540 | 500 | 1 month |
| 3 | 730540 | 500 | 3 months |
| 4 | 730536 730540 | 250 250 | 7 days |
| 5 | 730536 730540 | 250 250 | 18 days |

Example 4: 2'-O-Methyl Modified Oligonucleotides Modulation of Human ATXN3 by In Vivo A 2'-O-methyl modified oligonucleotide with the sequence GCUGUUGCUGCUUUUGCUGCUG (SEQ ID NO: 14), referred to herein as 10.1, was tested for its effects on splicing of human ATXN3 RNA in vivo. MJD84.2/SCA3 transgenic mice received one intracerebroventricular injection of 200 µg of the 2'-O-methyl oligonucleotide per week for three to four weeks, for a total dose of 600 or 800 µg. One control group received no oligonucleotide. Two weeks after the last injection, the mice were euthanized and RNA and protein were isolated from the cortex, cerebellum, and pons. The effects on human ATXN3 splicing were analyzed by RT-PCR and western blot as described in Example 2 and compared with the effects of 2'-MOE modified oligonucleotides (see FIGS. 3 and 4). The comparative results shown in FIG. 6 indicate that the 2'-MOE modified oligonucleotides tested were more potent than the 2'-O-methyl modified oligonucleotide tested in vivo.

Example 5: Tolerability of 2'MOE and 2'-O-Methyl Modified Oligonucleotides Targeting Human ATXN3

The tolerability of 2'-O-methyl modified oligonucleotides (ASO #9.2 and ASO #10.1) listed in Table 3 below was assessed in wild type mice. The 2'-O-methyl oligonucleotides target the complement of GENBANK accession number NT 026437.12 truncated from nucleotides 73524000 to 73574000 (SEQ ID NO: 1). The oligonucleotides listed in the table below are 100% complementary to SEQ ID NO: 1. The sugar moieties of the nucleotides are uniformly 2'-O-methyl modified and all internucleoside linkages are phosphorothioate linkages. The nucleobase sequences are listed in the table below. The start and stop sites associated with each oligonucleotide are the 5'- and 3'-positions, respectively, of the portion of SEQ ID NO: 1 that is complementary to the oligonucleotide. Wild type mice at 2.5 months of age received five intracerebroventricular injections of 100 µg of ASO #9.2 and ASO #10.1 (50 µg each) or of a 2'-O-methyl modified scrambled control according to the schedule shown in FIG. 7 for a total dose of 500 µg. A control group was similarly treated with an equal volume of PBS. As shown in FIG. 7, wild type mice treated with 2'-O-methyl oligonucleotides lost body weight as compared to PBS control.

The tolerability of 2'-O-methyl modified oligonucleotides (ASO #9.2 and ASO #10.1) listed in Table 3 below was also assessed in MJD84.2/SCA3 mice. MJD84.2/SCA3 mice at 2-3 months of age received five intracerebroventricular injections of 100 µg of ASO #9.2 and ASO #10.1 (50 µg each) or of a 2'-O-methyl modified scrambled control according to the schedule shown in FIG. 7 for a total dose of 500 µg. A control group was similarly treated with an equal volume of PBS. As shown in FIG. 8, MJD84.2/SCA3 mice treated with 2'-O-methyl oligonucleotides lost body weight as compared to PBS control.

TABLE 3

2'-O-methyl modified oligonucleotides for modulating ATXN3 expression in vivo

| ASO # | Sequence (5' to 3') | Corresponding 2'MOE sequence | Start site | Stop site | SEQ ID NO. |
|---|---|---|---|---|---|
| Scrambled control | CUGAACUGGUCUACAGCUC | n/a | n/a | n/a | 15 |
| 9.2 | GCUUCUCGUCUCUUCCGAAGC | 730536 | 26660 | 26680 | 13 |
| 10.1 | GCUGUUGCUGCUUUUGCUGCUG | 664568 | 36605 | 36626 | 14 |

Tolerability in the MJD84.2/SCA3 mice treated with 2'MOE modified oligonucleotide (COMPOUND 664568, COMPOUND 730535, COMPOUND 730536, COMPOUND 730537, COMPOUND 730538, COMPOUND 730539, COMPOUND 730540, and COMPOUND 730536+COMPOUND 730540) in Example 2, above, was assessed. As shown in FIG. 9, MJD84.2/SCA3 mice treated with 2'-MOE oligonucleotides generally maintained body weight and were, thus, well tolerated.

Observationally, animals treated with 2'MOE modified oligonucleotides recovered faster after intracerebroventricular injection as compared to 2'-O-methyl modified oligonucleotides. Furthermore, a higher dosage of 2'MOE modified oligonucleotides is tolerated as compared to 2'-O-methyl modified oligonucleotides (500 µg for 2'MOE modified oligonucleotides compared to 200 µg for 2'-O-methyl modified oligonucleotides).

Example 6: 2'MOE Modified Oligonucleotide Modulation of Human ATXN3 Transcript Splicing In Vivo Compound number 730540 was further tested for its effects on the splicing of human ATXN3 RNA in MJD84.2/SCA3 transgenic mice. One mouse received a single 500 µg intracerebroventricular injection of Compound No. 730540 at 80 days old, and euthanized after 2 weeks. Another mouse received a first ICV injection of 500 µg 730540 at 80 days and a second 500 µg dose 2 weeks later, with euthanasia 3 weeks after the second dose. After euthanasia, total protein was isolated from the cortex, cerebellum and brain stem. A western blot was run as described in example 1. After incubation for 3 hours with mouse SCA3-1H9, an IRDye® 800CW secondary antibody was added for 45 min. The intensity of the bands was quantified using Odyssey software in the 800 nm channel. The results are shown in the table below as raw intensity values, with the final column showing the percentage of truncated ataxin-3 relative to the total ataxin-3. The results show that treatment with Compound No. 730540, targeting exon 10, caused the production of truncated ATXN3 in the brainstem, cerebellum, and cortex.

TABLE 4

Results of western blot for ATXN-3 in various brain regions after mouse treatment with 730540

| Dose 730540 (mg) | Tissue | Human Mutant ATXN-3 | Mouse ATXN-3 | Human ATXN-3 ΔC-terminus | % skip in Human ATXN-3 |
|---|---|---|---|---|---|
| 0.5 | Brainstem | 101 | 49 | 26.5 | 20.8 |
| 0.5 | Cerebellum | 111 | 40 | 18.5 | 14.3 |

TABLE 4-continued

Results of western blot for ATXN-3 in various brain regions after mouse treatment with 730540

| Dose 730540 (mg) | Tissue | Human Mutant ATXN-3 | Mouse ATXN-3 | Human ATXN-3 ΔC-terminus | % skip in Human ATXN-3 |
|---|---|---|---|---|---|
| 0.5 | Cortex | 39 | 22 | 8.1 | 17.2 |
| 1 | Brainstem | 129 | 53 | 46.8 | 26.6 |
| 1 | Cerebellum | 107 | 31 | 27.1 | 20.2 |
| 1 | Cortex | 114 | 70 | 66.7 | 36.9 |

Example 7: 2'MOE Modified Oligonucleotide Modulation of Human ATXN3 Transcript Splicing In Vivo Compound number 730540 was further tested for its effects on the splicing of human ATXN3 RNA in MJD84.2/SCA3 transgenic mice at a lower dose. Six MJD84.2/SCA3 mice were cannulated and given an ICV dose of 500 µg of 730540 at 2.5 months of age. A second dose of 250 μg dose was given two weeks later, followed by a third dose a week later for a total dose of 1 mg modified oligonucleotide. Mice were sacrificed ~2.5 months after the final dose. After euthanasia, total protein was isolated from the cortex, cerebellum and brain stem, and analyzed by western blot as described in Example 1. Data were quantified with the Odyssey software as described in Example 6. The table below shows the percent of modified human ataxin-3 relative to total human ataxin-3 in the transgenic mouse. The control PBS-treated and scrambled control oligonucleotide column each represent a single MJD84.2/SCA3 mouse, while the 730540-treated column represents the average of six mice.

TABLE 5

Percent of exon-skipping observed in various brain regions after treatment with 730540 in vivo

| Brain region | PBS-treated control | Scrambled Control | Compound number 730540 |
|---|---|---|---|
| Brainstem | 5.6 | 5.3 | 42.0 |
| Cerebellum | 4.0 | 4.0 | 20.5 |
| Cortex | 5.6 | 5.5 | 43.6 |

Example 8: 2'MOE Modified Oligonucleotides Reduce ATXN3 Aggregates In Vivo

A dot blot filter trap assay was performed to assess the presence of ATXN3 aggregates in protein samples from the brainstem, cerebellum, and cortex of MJD84.2/SCA3 mice treated with Compound number 730540 and controls (PBS-treated and scrambled control oligonucleotide). Samples from wild type mice that do not express toxic human Ataxin 3 protein containing an expanded polyglutamine stretch (and therefore do not cause aggregates) were included as a negative control.

A 0.2 μm cellulose membrane was used to trap aggregates. After preequilibration with TBS, the membrane was placed in the dotblot device, washed with PBS, and 60 μL of protein stock at 0.5 mg/mL was added to 340 μL of PBS. Protein was transferred to the cellulose acetate membrane using vacuum and the membrane was blocked using a 5% milk solution. The membrane was stained overnight at 4° C. with SCA3-1H9 and for 1 hour with IRDye® 800CW, and then the intensity of the spots was quantified using Odyssey software in the 800 nm channel Intensity of the spots correlates to the number and size of aggregates in the sample. Table 6 provided below shows that aggregates were reduced in modified oligonucleotide treated samples as compared to control samples. Values represent the average of 2 mice for wild-type, 3 mice for the PBS-treated control, and 6 mice for the scrambled oligonucleotide control and Compound number 730540.

TABLE 6

Average relative intensity of dotblot for ATXN3 aggregates in brain region lysates after treatment with 730540

| | Wild type (−) control | PBS-treated control | Scrambled control | Compound number 730540 |
|---|---|---|---|---|
| brainstem | 4.1 | 114.6 | 105.0 | 58.2 |
| cerebellum | 4.3 | 152.8 | 133.0 | 76.7 |
| cortex | 5.6 | 113.5 | 105.8 | 79.5 |

Example 9: 2'MOE Modified Oligonucleotide Modulation of Human ATXN3 Transcript Splicing in SCA3 Patient Derived Fibroblasts Compounds 664568, 664569, 730538, 730539, and 730540 (described hereinabove in Example 1) were transfected in SCA3 patient-derived fibroblasts and tested for ATXN3 transcript splicing.

Fibroblast control (FLB73) and SCA3 (GM06153) cell lines were obtained from Coriell Cell Repositories (Camden, USA) and maintained in Minimal Essential Medium (MEM) (Gibco, Invitrogen, Carlsbad, USA), containing 15% fetal bovine serum (FBS) (Clontech, Palo Alto, USA), 1% Glutamax (Gibco), and 100 U/ml penicillin/streptomycin (Gibco).

Transfections of modified oligonucleotides were performed as described previously (Evers et al., 2013). Briefly, fibroblasts were re-plated the day before transfection. Modified oligonucleotides were diluted to 200 nM in MEM medium without supplements containing 0.3% lipofectamine (Life Technologies, Paisley, UK) for fibroblasts transfections. The transfection mixture was incubated on the cells for 4 hours, after which a three times volume of normal growth medium was added. Cells were harvested one day after transfection for RNA analysis, or 2 days after transfection for protein analysis.

RNA isolation was performed by detaching cells by trypsinization (Life Technologies) and subsequently spinning down. RNA was collected from the cell pellets using the Reliaprep RNA Cell Miniprep kit (Promega, Madison, USA) according to manufacturer's instructions. Further RNA purification was performed by using the PureLink RNA mini kit (Thermo Fisher scientific) in accordance with the manufacturer's protocol, using a 15 minutes. RNA was eluted in 80 μl nuclease free water.

RT-PCR was performed as follows: For cDNA synthesis, 500 ng of RNA was used as input for the Transcriptor First Strand cDNA Synthesis Kit (Roche, Mannheim, Germany). The cDNA synthesis reaction was performed using oligoDT primers according to manufacturer's instructions for 45 minutes at 50° C. and stopped for 5 minutes at 85° C. PCR was subsequently performed using primers described in Example 2 with 1 μl cDNA as input. The PCR reaction was set up with 0.25 mM dNTPs, 1U Faststart Taq DNA polymerase (Roche) and 10 μmol forward and reverse primers (Eurogentec, Liege, Belgium). PCR cycling was started with 4 minutes initial denaturation at 95° C., followed by a total of 36 cycles with 30 seconds of denaturation at 95° C., 30 seconds of annealing at 59° C., and 1 minute extension at 72° C. At the end of the program a final elongation step of 7 minutes at 72° C. was used. PCR products were separated by electrophoresis on 1.5% agarose gel containing 0.002% ethidium bromide. Bands of skipped products were excised from the gel, purified using a DNA extraction kit (Machery Nagel, Duren, Germany) according to manufacturer's instructions and the sequence was obtained by Sanger sequencing (Macrogen, Amsterdam, the Netherlands).

Protein isolation and Western blot was performed by trypsinization and centrifugation of cells, after which the pellet was dissolved in Radioimmunoprecipitation assay (RIPA) buffer. Next, protein lysates were incubated in a head-over-head rotor at 4° C. for 30 min. Protein concentration was determined using the bicinchoninic acid kit (Thermo Fisher Scientific, Waltham, USA), with bovine serum albumin as a standard. Protein samples were separated using 10% sodium dodecyl sulfate polyacrylamide gel electrophoresis (SDS-PAGE) with Laemmli sample buffer after boiling for 5 min at 100° C. Proteins were blotted onto a nitrocellulose membrane using the Transblot Turbo system (Bio-Rad, Hercules, USA), for 10 minutes at 1.3 A. Blocking of membranes was done with 5% low fat milk powder in tris buffered saline (TBS) for 1 hour at room temperature. Membranes were stained using mouse anti-ataxin-3 1H9 (Abcam, Cambridge, UK) at 1:5000 dilution and rabbit anti-GAPDH (Abcam) 1:50.000 overnight at 4° C. Blots were washed and incubated for 1 hour with Odyssey secondary antibodies, goat-anti-mouse IRDye 680RD or goat-anti-rabbit IRDye 800CW (LI-COR Biosciences, Lincoln, USA) at a 1:5000 dilution. Membranes were scanned using the Odyssey infrared imaging system (LI-COR). Protein bands were quantified with the Odyssey software version 3.0 using the integrated intensity method.

RT-PCR and western blot analysis showed that compounds 664568, 664569, and 730540 were capable of inducing exon 10 skipping. A shorter Ataxin-3 transcript (Δ exon 10) and protein (Δ C-terminus) were observed (see, FIGS. 10 and 11, respectively). Removal of exon 10 from the Ataxin-3 pre-mRNA results in a modified Ataxin-3 protein lacking the toxic polyglutamine (polyQ) repeat. A reading frame shift occurs, resulting in a stop codon right at the start of the out-of-frame exon 11. As a consequence, the resulting Ataxin-3 protein is truncated to amino acid 291, thus lacking the C-terminal region.

Compound 730540, which was most efficient at inducing exon skipping, targets a sequence region containing a SNP (rs12895357) NM_004993.5 (ATXN3):c.916G>C (p.Gly306Arg) associated with the expanded allele in the cell-line used here, and in over 70% of SCA3 patients (Gaspar et al., 2001).

Example 10: 2'MOE Modified Oligonucleotide Modulation of Human ATXN3 Transcript Splicing In Vivo Compounds 664568, 730538, 730539, and 730540 (described in Example 1) were tested in MJD84.2 mice. The MJD84.2 mouse contains the full human ATXN3 gene with 84 CAGs including introns and flanking regions, making it a suitable SCA3 rodent model to assess human ataxin-3 splicing events in vivo. Sequencing analysis showed that the human ATXN3 gene in this mouse also contains the SNP (rs12895357). Modified oligonucleotides were injected as a single 500 µg ICV bolus in anesthetized hemizygous MJD84.2 mice to assess efficacy. RT-PCR and Western blot was performed as described in Example 9. Two weeks after the injection, exon skipping was analysed in cortex and cerebellum (FIG. 12). Sanger sequencing confirmed that the shorter ATXN3 RNA was the result of exon 10 skip of the human transcript. In line with the transcript modification, a modified Δ C-terminus ataxin-3 protein of approximately 36 kDa in size was observed in the treated animals (FIG. 13). Protein modification appeared more efficient in cortex than cerebellum. In the untreated animals, an ataxin-3 protein of similar size as Δ C-terminus ataxin-3 was observed as well, perhaps indicating the truncated ataxin-3 protein is a naturally occurring isoform or cleavage fragment in these mice.

Example 11: Prevention of Nuclear Accumulation with 2'MOE Modified Oligonucleotide The effect of treatment with compound 730540 on expanded ataxin-3 aggregation in SCA3 mouse brains was examined by immunofluorescence using the 1H9 monoclonal antibody. Nuclear accumulation of expanded ataxin-3 has been shown to aggravate neurodegeneration and formation of aggregates in vivo (Bichelmeier et al., 2007), and is therefore a useful marker to assess ataxin-3 toxicity.

MJD84.2 mice were treated as described in example 7 with a total dose of 1 mg of compound 730540 ICV. Mice were sacrificed at ~5.5 months of age. Sectioning of paraformaldehyde fixed mouse brains was performed using a Leica CM3050 cryostat for four control and three compound 730540 treated mice. Sagittal sections of the right hemisphere were obtained at 25 µm thickness and immediately transferred as free floating sections to PBS containing 0.02% sodium azide at room temperature. Sections were stored at 4° C. until staining Prior to staining, sections were washed three times in PBS with 0.2% triton-X100 for 10 min. Sections were then incubated with M.O.M. mouse IgG blocking reagent (Vector Laboratories, Burlingame, USA) for 1 hour. Sections were washed and incubated overnight at 4° C. with primary antibodies diluted in M.O.M. protein concentrate diluent (Vector Laboratories). Primary antibodies used were: mouse anti-ataxin-3 1H9 1:1000 (Abcam, Cambridge, UK) and rabbit anti-tyrosine hydroxylase 1:500 (Santa Cruz biotechnology, Dallas, USA). For assessment of modified oligonucleotide distribution, a rabbit antibody binding the phosphorothioate backbone of modified oligonucleotides was used at 1:20.000 diluted in 1% normal goat serum. After washing, sections were incubated with secondary antibodies, goat anti-mouse-alexa Fluor 594 or goat anti-rabbit-alexa Fluor 488 (Life technologies, Paisley, UK) at 1:500 dilution. Sections were mounted on superfrost plus coated microscope slides (Fisher Emergo, Landsmeer, Netherlands), coverslipped using EverBrite hardset mounting medium containing DAPI (Biotium, Hayward, USA) and cured overnight prior to fluorescent microscopy using a Leica DM-5500 fluorescent microscope at 10× magnification.

Tyrosine hydroxylase staining was used to localise the substantia nigra in sagittal brain sections. Fluorescent images of substantia nigra were analysed using ImageJ (version 1.48) (Schneider et al., 2012). Images were converted to 8 bit and the substantia nigra was automatically selected using a region of interest based on positive tyrosine hydroxylase green fluorescence (threshold 25-254). Within this region, ataxin-3 nuclear staining was determined by using the analyse particles function (circularity 0.15-1.00) based on red fluorescent staining (threshold 35-254). Background fluorescence (intensity 35) was subtracted and the average fluorescence intensity per cell was subsequently used to represent intensity of nuclear ataxin-3. Identical analysis values were used to analyse all images. Over 400 and 1300 individual cells were assessed for compound 730540 treated mice and control treated mice, respectively.

Ataxin-3 nuclear localisation was readily seen in the substantia nigra. The intensity of ataxin-3 nuclear localisation in the substantia nigra was markedly reduced in mice treated with compound 730540 when compared to animals treated with control (FIG. 14).

Example 12: Ataxin-3 Δ C-Terminus is Capable of Binding Ubiquitin Chains

Due to the frameshift induced by exon 10 skipping, the ataxin-3 Δ C-terminus protein lacks the third UIM. The ability of ataxin-3 Δ C-terminus to bind ubiquitin chains was investigated. A U2OS 2-6-3 celline (Janicki et al., 2004) where transfection of an mCherry-LacR-RNF8 construct led to localized ubiquitilation of chromatin (Luijsterburg et al., 2015) was used. Colocalization of ataxin-3 to the ubiquitin conjugates at the LacO array can be used as a marker for ubiquitin binding activity of ataxin-3.

GFP tagged ataxin-3 constructs were obtained as follows: PCR products were generated with primers flanking the full length ATXN3 transcript (see Example 2) using modified oligonucleotide transfected fibroblast cDNA as template. Full length or exon 10 skipped products were gel extracted, purified and ligated in the pGEM-T Easy vector (Promega). Mutations of the UIMs were generated using the Quick-Change II Site Directed Mutagenesis kit (Agilent Technologies, Waldbronn, Germany) as described previously (Evers et al., 2013). Expanded ataxin-3 was obtained by genesynthesis (Genscript, Piscataway, USA), a mixture of 71 CAG and CAA codons was generated to improve stability during the cloning process. Constructs were then subcloned into the PacGFP-C1 vector (Clontech, Mountain View, USA) using notI digestion, resulting in an N-terminally GFP tagged ataxin-3 protein expression following transfection in cells. The mCherry-LacR-RNF8 construct has been described previously (Luijsterburg et al., 2012). All constructs were verified using Sanger sequencing.

To assess the ubiquitin binding capacity of modified ataxin-3 human U2OS 2-6-3 cells with LacO repeats integrated in the genome (Janicki et al., 2004) were grown on glass cover slips. Cells were transfected with both mCherry-LacR-RNF8 (Luijsterburg et al., 2012) and GFP-ataxin-3 constructs. The cells were fixed the following day and the glass slides were mounted on microscope slides with Everbrite mounting medium with DAPI (Biotium, Corporate Place Hayward, Calif., US). The cells were subsequently imaged at 63× magnification using a Leica DM-5500 fluorescent microscope. Fluorescent images were obtained for a minimum of 50 cells (2 replicate transfections) positive for both RNF8 and ataxin-3 fluorescent signals. Due to the LacR fusion, the RNF8 protein construct localises to the lacO repeat of the genome and results in ubiquitination of the local histone. By drawing a line region of interest across the RNF8 localised at the array, the increase in GFP-ataxin-3 at the same location could be determined using the LAS AF Lite software (Leica Microsystems). The background GFP signal was subtracted from the peak value to obtain the increase of ataxin-3 constructs localisation at the assay.

Ataxin-3 with either 10 polyglutamine repeats or 71 polyglutamine repeats readily colocalized at the array (FIG. 15). Ataxin-3 with all 3 UIMs inactivated by point mutations (L229A, L249A, and L340A) (ATXN3 ΔUIMs) colocalized to a significantly lower extent, confirming the specificity of the assay. Values represent >40 cells obtained from two independent experiments. Ataxin-3 Δ C-terminus colocalized at the array to a similar extent as wildtype ataxin-3, indicating that the ubiquitin chain binding capacity of the protein was fully retained despite lacking the third UIM.

The invention claimed is:

1. An oligomeric compound comprising a modified oligonucleotide consisting of 15-25 linked nucleosides, wherein the modified oligonucleotide has a nucleobase sequence comprising 16, 17, or 18 contiguous nucleobases of SEQ ID NO 11, wherein at least one nucleoside of the modified oligonucleotide comprises a modified furanosyl sugar moiety that is not a 2'-O-methyl modified furanosyl sugar moiety.

2. The oligomeric compound of claim 1, consisting of the modified oligonucleotide.

3. The oligomeric compound of claim 1, wherein the modified oligonucleotide is single-stranded.

4. The oligomeric compound of claim 1, wherein at least one internucleoside linkage of the modified oligonucleotide is a modified internucleoside linkage.

5. The oligomeric compound of claim 4, wherein each internucleoside linkage of the modified oligonucleotide is a modified internucleoside linkage.

6. The oligomeric compound of claim 4, wherein the modified internucleoside linkage is a phosphorothioate internucleoside linkage.

7. The oligomeric compound of claim 5, wherein each internucleoside linkage of the modified oligonucleotide is a phosphorothioate internucleoside linkage.

8. The oligomeric compound of claim 1, wherein at least one nucleobase of the modified oligonucleotide is a modified nucleobase.

9. The oligomeric compound of claim 8, wherein the modified nucleobase is a 5-methylcytosine.

10. The oligomeric compound of claim 1, wherein each nucleobase of each nucleoside of the modified oligonucleotide is either an unmodified nucleobase or is a 5-methylcytosine.

11. The oligomeric compound of claim 1, wherein each modified furanosyl sugar moiety is a bicyclic sugar moiety.

12. The oligomeric compound of claim 11, wherein the bicyclic sugar moiety comprises a chemical bridge between the 4' and 2' positions of the sugar, wherein the chemical bridge is selected from: 4'-CH(R)—O-2' and 4'-(CH$_2$)$_2$—O-2', wherein R is independently H, C$_1$-C$_6$ alkyl, or C$_1$-C$_6$ alkoxy.

13. The oligomeric compound of claim 12, wherein the chemical bridge is 4'-CH(R)—O-2' and wherein R is H, methyl, or —CH$_2$—O—CH$_3$.

14. The oligomeric compound of claim 1, wherein the modified furanosyl sugar moiety comprises a 2'-O-methoxyethyl group.

15. The oligomeric compound of claim 1, wherein each nucleoside of the modified oligonucleotide comprises a modified furanosyl sugar moiety.

16. The oligomeric compound of claim 15, wherein each modified furanosyl sugar moiety comprises a 2'-O-methyoxyethyl group.

17. A pharmaceutical composition comprising the oligomeric compound of claim 1 or a salt thereof and a pharmaceutically acceptable diluent.

18. A method of modulating splicing of Ataxin-3 pre-mRNA in a cell comprising contacting a cell with an oligomeric compound, wherein the oligomeric compound comprises a modified oligonucleotide having a nucleobase sequence comprising 16, 17, or 18 contiguous nucleobases of SEQ ID NO 11, wherein at least one nucleoside of the modified oligonucleotide comprises a modified furanosyl sugar moiety that is not a 2'-O-methyl modified furanosyl sugar moiety.

19. The method of claim 18, wherein the modified furanosyl sugar moiety comprises a 2'-O-methoxyethyl group.

20. The method of claim 19, wherein each nucleoside of the modified oligonucleotide comprises a modified furanosyl sugar moiety comprising a 2'-O-methyoxyethyl group.

21. The method of claim 18, wherein the cell is in vitro.

22. The method of claim 18, wherein the cell is in an animal.

23. A method comprising administering to an animal having or at risk for developing SCA3 a therapeutically effective amount of an oligomeric compound of claim 1 wherein the administering reduces the number and/or volume of aggregates in brain tissue.

24. The method of claim 23, wherein the brain tissue is selected from the group consisting of brainstem, cerebellum, and cortex.

* * * * *

SEQUENCE LISTING

```
<160> NUMBER OF SEQ ID NOS: 15

<210> SEQ ID NO 1
<211> LENGTH: 50001
<212> TYPE: DNA
<213> ORGANISM: Homo sapien

<400> SEQUENCE: 1
gtttcatcaa accgctgcta cctccccgtc tcccacacaa tttatgggac ttctaagttc      60
cctctaaagg gtccgaacac ctacactggt aacaagccac ctggatttga atcctggcaa     120
gacaacttac tatctgacct tggacattgt gctgttctta acctctccgt gcctcggttt     180
cctcatgtgt atgaataaca tcaacaccta catcaaagtt tgctgtatta aatttgataa     240
tatatgcaaa gcatttagaa aagtgcctag ctcatagaaa gccttatgta aatattaact     300 atcattttt ttctttttg gggtggtggg ggaggggttt cgcttttgtt gcccaggctg      360
gcgtgcaatg gcacgatctc ggctcaccac aacctcggcc tcccggttc aagcgattct      420 cctgcctcag cctcccgagt acctgggatt acaggcatgc accaccacgc ccgggtaatt     480
ttgtattttt agtggagacg gggtttctcc atgttggtca ggctgatctc aaactcccga     540
cctcaggtga tccgcccgcc tcggcctccc aaagtgctgg gattacaagc gtgaagcacc     600
tcgcccggcc tagctatcat ttttatacaa gtgctgggtt ttgggagaat gtaatgatgg     660
cttttttctt actaaacttt cagtgcagga ggaggagaaa gaaagtaaat agttatatga     720
acacagtaga aagtcaaagt ggaaaacaaa aagaacatag aacccaggtg agcggtccag     780 acctccccc agaaacctaa gaatccatag aaatgggtgg gaagcggaga agatcctcca      840
```

```
gacagcaggt ggcgatgtag catcccccag aaggcccgct aacagaagct aggaggacgc    900
gctaccaagg tcacgtgtcc ccggcgttca ctcgctcttc gcttcacgac actcgcatcc    960
tcacgggtga ttggtctgcg tgcggcacgt gggcggggta ccggggcggg ccggggaggg   1020
gcggggtggg cggaggagag gggcaggggg cggagctgga ggggtggtt cggcgtgggg    1080
gccgttggct ccagacaaat aaacatggag tccatcttcc acgagaaagt gagtgtccgc   1140
gttcggtggg gagctgtctg ccgcgcggtg gcgggcgtgg agcgcggcat caccgcctct   1200
cggagggctg ggtgggggccc gagtcgcccc catgccgatc tcgcccggcg aggggcgacg   1260
ccgcagcctc ccgcctcctc ggctcgagga ggggagcatc acctacgccc ctacttcccc   1320
cgcggccccc gccctgggag ccgggaggga gtatgggcgg ggccggggc gtctcgggac    1380
acgggagtgg ggtggcgccc agtgggtttg cttctgcctt tctccgtcac tttccatcgc   1440
ttttcggagg attccttcac ccctccccaa tccttccctc tccctagggt ctagctagag   1500
tcatctctgg gacacctccc tcaacccctc ctaccctaat cctggcagaa ttaacttttc   1560
ctcctccgga ctgctcaatt ctatattgga gtcttcccta cacgtagatc tttggggtct   1620
tgttcgtgtc tttcccctgc actaggtccg cgagcctccc gagggaggag accttggctc   1680
gcccactgta gggcctgaca tttaggaagt gaagtaggaa acccggcgtg cccctaaaca   1740
gggaagtcgt cacaagagtt tttattacgg gatgtttggg tttggtttct tttggtactc   1800
ccatctttcc ggagcaggcg gccagctttg tttttaggta ttaggagtgg actgggatga   1860
ttttgttgta gtctgcctag cctgctgtcc ctttaactct tccgtgacca tgcacttgaa   1920
gatactgttt gtgatatgta aagaaactcc tcgtttctct catactatta tccagccatt   1980
tgtgtgtgag tgaagccttc cccaggacag ctttggcaca tggtatcatg tttcataata   2040
gtttcgtgtt tggaaagagt tgctggtaag gctgttattt aataggagga gcaaagggtt   2100
tttgttttat aaatactta taaatgatca tttatcccag acatttaaaa ttcacacaca    2160
cacaacaaat aaagcaaaga caaaagaata catttaccaa atgtaaatct gtagcataaa   2220
tttttttaa ttttattttt aaagatgggg tctcattctg tcacccaggc aggtgtgcaa    2280
tggagagatc atggctcact gcagccttga tctcctaggc acaagcgatc ctcccgcctc   2340
tgcctccaga gtagctggga ctacaggtgc atatcgccag gccaggtaa tgttttggg     2400
agagacgggg tctcgctgtg ttgcccaggc tggtctcgaa ctcctggact caggtgattc   2460
tcccacctcg gcctctcgaa gtgctgtgat tacaggcgtg agccactgtg cctggaacaa   2520
attgttaagt acaatgcttt tcattgtaga aaacatctcg gaaactttg aaataggctg    2580
atgttcagtg ggggaggaag gactcagtcg tatagttgtc actaattttt tgacttgatt   2640
gacatgactc gtaaatcata gacaatagag atttggttgc ttggctgagt agagtgcgtg   2700
aaaaatacac acgtactttt tttttttttt ttttgagatg gagtttggct cttgtcaccc   2760
aggctggagt gcaatggcgc catcatggct cactgcaacc tccgcctccc cgttcaagcg   2820
attctcctgc ctcagtctcc ccagtagctg agattacagg cgcccgccac cacgcccagc   2880
taattttgt attttagta gagacagggt ttcaccatgt tggccaggct ggtctccaac     2940
tcctgacagg tggtccgccc gcctcggcct cccaaagtgc tgggattaca ggcgtgagcc   3000
accgcacccg gccatatttt tgttattaat tttcaaaggc tttggtgtgg gaccacattt   3060
caacatggaa ggccttaaac atgttccaca ctacttcctg agaattagac aagattttta   3120
acaatattgt tacctagttg ggacacattt gtactgaccc atgggatgaa aaaaagctga   3180
```

|  |  |  |  |  | |
|---|---|---|---|---|---|
| gtgctagcct | agtgaaaatc | tacttacccg | aaagaaatcc | ctcttagtct | gggtgcagtg | 3240 |
| gctcacacca | gtgctttggg | aggcccagac | gggcggatca | tgaggtcagt | agtttgagac | 3300 |
| cagcctggcc | aacatggtga | aaccccgtct | ctactaaaaa | tacaaaaaat | tagccaggtg | 3360 |
| tggtggcagg | cgcctgtaat | cccaggtact | ctggaggctg | aggcaggaga | attgcttgaa | 3420 |
| cccgagaggc | agaggttgca | gtgagccgag | accgtgccac | tgcacttcag | cctgggcaac | 3480 |
| agagcgagac | tccgtctcaa | aaaaagaaa | aggaaaaaag | agtccctctt | aattatcagc | 3540 |
| atgtgtatag | gcctacagat | acttcaggaa | tacctttacc | attatcatca | acttgtatct | 3600 |
| acatagcatg | tgaagattca | acaatttagt | tttttgggcg | tcctcaagag | tacgcaccta | 3660 |
| taaccatatg | gcccaattgt | taatctccta | tacagtccat | tctgggaatg | tttgggctta | 3720 |
| ctgtgccatt | tttccgttca | ctgccttccc | ctctgcaata | tacctttaac | ccttgctagg | 3780 |
| tcctgggttt | ggagagccag | agaaccaact | ttggccctaa | agaagctgtg | taggtagcaa | 3840 |
| tatctgccta | cgaagggcct | tgcaaccatt | tcctcttgga | accttggttt | cctctttctg | 3900 |
| agtagtcact | ttgagtaccc | tttattaagt | tagaatgtaa | aaacagtttc | tcactgatat | 3960 |
| atctgcagtg | cctgagagag | ggcctggcac | agagtaagta | ctcaataaat | atttgaatgg | 4020 |
| ggccgggcgt | ggtgagacct | gtctctacaa | gaatgaacaa | aattagctgg | gcgtgttagc | 4080 |
| acatgcctgt | agacttggga | ggctgaggtg | ggaggattgc | atgagtctgg | gaggtcgagg | 4140 |
| ctgtagtgag | ccatgatcgc | accactgcac | tccagcctag | gggacagagc | aagatcctgt | 4200 |
| ctcaaaagaa | aaaatgtat | atatttgaat | ggataaagag | atggctttga | gtttctgaga | 4260 |
| tatatatggt | gctgtttatc | taaagtaaac | aagttttctg | taaatatttt | aaggctttgc | 4320 |
| aggccagctg | tagtctctgt | cacacattct | tatttgtgca | tgttttcccc | aaccatgtaa | 4380 |
| aaatgtaaag | tgcattctta | gctactgggg | caggttgaat | ttggcccatg | ggctagagtt | 4440 |
| tgccaacccc | taacttaaac | ctttgtacta | actttatgac | cactactgga | ttttgttgt | 4500 |
| tgtttgtttt | agttctggtg | cctgcttgt | tttttttttt | tttttaatc | ctcttgctga | 4560 |
| tgtttcttgg | tgcagttact | gtgccatttg | tattggtgct | tttaatgtaa | tgcaaactgg | 4620 |
| taataatatc | taaacttgct | ggggttgtac | ataaaattat | tgaaaagatt | gaaaagatgc | 4680 |
| tgagcattga | ctctgtggca | ttcattatgc | ccttttgtga | ttgctggatt | ttagccatct | 4740 |
| ttaggacatt | tgagctttag | gagaagccaa | attctgtata | aatgacttga | agtgctaata | 4800 |
| gcacaggttt | tgaaacctct | gcctgggttt | gagtctcagc | tctgcctttt | actacctgtg | 4860 |
| tgatcctgag | caagttactt | agtatccctg | tcctctagtt | tcctcctctg | tagtgtgggg | 4920 |
| ataataacat | agacataacc | tgagagttag | agtgtagaga | aggctccctg | gcagatagtg | 4980 |
| ctgtagaagt | actggccatt | gccattactc | aggtgcttgt | gtttgctgaa | cctcatagta | 5040 |
| agggctcgga | gagcactaag | aggaggtgag | aaatgctgct | agattgacag | cttgtcccca | 5100 |
| gatagcccat | tcccgagagc | accttaggtt | tatacctgat | ttgtgttgta | gttagtagtg | 5160 |
| tctctggtaa | tttgaactag | tttcaggttg | gtcttgaaaa | cctggggagg | ttgggggtaa | 5220 |
| atgatttggt | agcagttctc | ttttgtgatt | ttatacatta | tctttgtaga | actgcagttt | 5280 |
| gctaattctc | tgagcccaac | acaatgaagt | ctgggcctaa | aatcatagaa | tttctttat | 5340 |
| tttttttttt | gtttttaatt | tatttattcc | ctccctccct | cctttcttcc | tttcttcctt | 5400 |
| ttctttcttt | ctttccttcc | ttccttcctt | ctttcttttc | tttctttctt | ttctttcttt | 5460 |
| ggagtctcac | tctgtcacca | ggctggagtg | cagtggcacg | aacttcttc | agagtctcac | 5520 |
| tttgtcacca | ggctggagtg | cagtggcgcg | aactcagctc | actgcaacct | ccgtctcctg | 5580 |

```
agttcaagag attctcctgc ctcagcctcc cgagtagctg ggactatagg catgtgccac   5640
catgcccagc taattttctt atttttagta gagacgaggt ttcaccatgt tggccaggat   5700
ggtcttgatc tcttgacctc gtgatccacc tgcctcagcc tcccaaagtg cggggattac   5760
aggcgtgagc taccacgccc agcctatttt ttattttttg aggcagagtc tcactctgtc   5820
acccaggctg gagtgcagtg gtgcaatctc agctcactgc aacctccgcc tcctgggttc   5880
aggtgattct cctgccttag cctcctgagc acctgggact acaggcgcct gccaccacac   5940
ctggctaatt cttatatttt tagtagaggc ggggtttcac catgttggcc aggctggtct   6000
cgaactcctg atctcaagtg atcaacctgc cttggcctcc caaagtgctg gaattacagc   6060
catgagccac catgcccagc caaatcatga gatttcaata ccgctgaact ttgattatgg   6120
caaagtgaac ttctgctttg attaaagctt gatgagagag gtggctgggg atagtttgag   6180
ataagggcaa ggcaggaaaa tgcataatct tacgtgggct cattgtcatt gtacaattct   6240
tttggtccat gtggaatttg atccgtccta tgacttaagt tatgtttatt tttgttttta   6300
tttttattta ttttgtgtct ttttgagaga catgatgttg ctctgtcacc tgggccagaa   6360
tacagtggca aatcttagc tccgtgtagc cttgaactcc tgggctcaag tgatcctccc   6420
acctcagccc ctcaaacagt tgagattata gtatgaacca ctgtgcctag ccttaagtga   6480
tttttaaatt tgtactgaac agtttgtcct ttccttccat taaatcatat tagaagtaca   6540
gaacttgata tttcctgtag caatacagtt tttctttgat gaagtttgat ttcaagtact   6600
tatttttcat aatttaaagc tatttttat agagagaatt ttaatcaaat atttggatgt   6660
cactattgct atatatggta ttaagtatgg tgaccatagt ttgtaaactc caaactgaca   6720
gcaagacagg aaatttgtgt tagcaaaggc tttttttctta ctgtttgaat ttttttaaaaa   6780 ttagatacaa tacagagagg agcacacaaa tcattaagag tacagctcag cgaattttca   6840
cacagtgaac atgtgtaaac agcaagtaac aaaagattta cctgcatcct ataacctccc   6900
attattccct tttctaggta ctgtctctcc actgcattcc caccaaatat aaccactatg   6960
ctgaattctg acatcataaa tgagttttgc ctgattttga gcttttgtga ctggaagtgt   7020
acagtgtata tacccttttcg attctgtcct ctttagttta ccattgtttg agaaatttat   7080
ccatactgtt ccagaattaa ctactgttaa ttattgttaa ttaactactg ttgtagttaa   7140
ttcatcctca ttgttatcta gtattctttt gtgagtaaac acaatttcca ttctactgtg   7200
atcccagcta tccatttggg tcgtttccag tttggggtcc attacaaata gtaatgctat   7260
ctgtaatgct atttttgtatt actacaaata gtaatgctat ttgtggcaca aaaatactgc   7320
ttttgtgaac attcttatac atgtcttttg atgaatgtat gtttgcattg ctgttgttta   7380
cattatgtac ctagtaatgg aattgctaga tcataggaga tgtatatatt aagctttagt   7440
ggatgcatta cataattatt agttattatt ggttatacca atttatcctc tcatcagtag   7500
tatacaacag tttctgtatc tctaatctcc aacattttag ccattttaga gtttgtgtac   7560
taacacattg tggttttaat ttacatttcc ctgatgacta ataaagttga gtacctcttt   7620
tgtgttcttt atagccattt gactgtcttg tgaagtgctt gtttgtcttg cctatttttc   7680
ttttctttct ttcttttttct tccttccttc ctttcttttct ttcttctttc tttccttcct   7740
tcttttcttt ctttctgtct ttctttcttg tcttttcttgt ctttctgtct ttcttggtct   7800
tgccctgtca cccatgctgg agtgcagtgg tgcagtctca gcttactgta gcctcgacct   7860
ttttggggct caagttatcc tcctttctca gcctcccaag aagctggact acaagcacgc   7920
```

```
accaccatgc tcagttaatt ttttattttt tgtagaaatg gggtttcacc atgttgtcca    7980
ggctggtctc aaacttctgg gctcaagtaa tcctcctgcc ttggcctccc aaaatgctgg    8040
gattacaggc atgagccacc gcagccagcc ttggctattt ttcaaaagga tataagtaga    8100
acatctgtat atcccttcaa tttgcatatt attcagtaag agttgcactc tggtagtaga    8160
aatatataag gaggagaaag aagtggaaac aaaaagtcta ttctcatgag aagacttggg    8220
ggatagtgtt ctctctagct ccaagctact tattccttac gaaaagttga agataaactt    8280
atctcagact gaggctgtct caatgttgtc ttcctattcc attatacaca tataacccat    8340 attttttca  ccagctgaat tttgctccta gaaaattgat tcatcaggaa aaatatccgt    8400
cttgcaaggt ggttctcttt agagtctgct gtgtgacata gctcaggaca aattgtgtga    8460
tgtcagatag gttgggttaa ggaatagacc ttattgggga agagagaac  ttggagggcc    8520 aaggttagca ggagaaggaa atgttctctc atctgccgtc aattcaggga ggggcaaacc    8580
tggtgtctgt gttcacaggg agggatccat ccatctgtga ttctcccttc ttatcaggta    8640
gcatgggaaa gctacactgt tgcggggagg agggtcacac gcaggctact tagtaccagg    8700
caccctggac ttggattcag gttgccagtt gtgtgagaaa ctgcccagca cctgaaggcc    8760
ctgaacccat gagaagttgt acctacctcc catgaggagg aatcctgtca tcccatggga    8820
gctgagcttg ggtgcagtcc ctcttgctgg cttgtccagg agtgagctcc agggttgttt    8880
gggacagttc tgctcattgc tttacactgt gtatacatta tctgtagagt tccatgaaga    8940
gaacttcagc actgtaactg caagttttaa catggaacag aatttttctc acctgtatta    9000
attcttaaga tttgaagttc tatcaacaag catttagatt gtgtggagat tttttttattt   9060 ttattttgg agacagagtc ttgctctgtt acccagactg gagtggcagt ggcatggtct    9120
tggctcactg caggctctac ttcctgggtt caagcgattc tcatgcctca gtgtcctgat    9180
tagctaggac tacaggtaca caccaccatg ctggctaatt tttgtatttt tagtagagac    9240
gaggtttcac cgtattggtc aggctggtct cgaactccca gcctcaagca gtccacccac    9300
ctcggcctcc caaactgctg ggattacagg tgtgagccac catgcttgac tgacatcatc    9360
atgttaaaag aataaatgtt ctaggagct  gggcacagtg tcatgtttct gtagttctag    9420
ctgctcggga ggctgaggca ggaagatccc ttgagccctg gagttcaagt ccagcctggg    9480
caacatagtg agatctcttt ttttaaataa ataaataact gttctaggga ctaaaatttc    9540
ctttcaccat tagtaattta ctgtagaatc tccaagaatg aacttatttt aggtactgaa    9600
aatgagggag actaaatgtt ttatacagta gtttttagta aaatatgaga tttgatgcat    9660
ttgatagatg atgtttgttt aaaataattc ttaaatttt  gatcatgtaa ttatagtttc    9720
attaatggta gatttgtaaa ataaatgtta ccaaatgaaa atgcatgtac ctatgttaat    9780
tatccttatc taaagctgaa agttcagttc aactatgtta aaacatagta ggggcctggc    9840
agggtggctc ttgcctgtaa tcccagaact taggaggcc  aaggtgggca gatcacgagg    9900
tcaggagatc gagaccatcc tggctaacat tgtgaaaccg tatcgctact aaaaatacaa    9960
aaaattagcc gggcatggcg gtgggcacct gtagtcgcag ctacttggta ggctgaggca    10020
ggagaatggc gtgaactcag gaggcagagc ttacagtgag ccgagatcat gccactgcac    10080
tccaggctgg gtgacagagc aagactccat ctcaaaaaaa aaaaaaagt  tggccaggtg    10140 tggcggctca cacctgtaat cccagcactt tgggaggccg aggcaggcgg atcacaagat    10200
caggagtttg agaccagcct ggctaacaga gtgaaaccct gtatatacta aaaatacaaa    10260
aattagccag gcatggtggt gcatgcctgt agtcccagct acttgagagg ctgaggcagg    10320
```

```
agaatcactt gaacccggga ggcggaggtt gtggtaagct gagattgctc cactgcactc   10380
cagcctggac aacagagcaa gactctgtct caaaaaaaaa aaaaattaat gattaaatta   10440
tttaggggag ccgggcgcag tggctcacgc ctgtaatccc agcactttgg gaggccaagg   10500
cgggcggatc acgaggtcag gagatcaaga ccatcctggc taacacagga tgaaaccccg   10560
tctctactaa aaatacaaaa atttagccgg gcgtggtggc gggtgcctgt agtaccagct   10620
actcgggagg ctgaggcagg agaatggcat gaacccgggt ggcggagctt gcagtgagcc   10680
aagatagcgc cactgcactc cggcctgggt gaaagagtga actccgtctc aaaaaaaaa   10740 aaaaattat ttaggggaag atactataca attctgttta acaagtcaca ttttaatttt   10800
ttcttttgga aatattagca agaaggctca ctttgtgctc aacattgcct gaataactta   10860
ttgcaaggag aatattttag ccctgtggaa ttatcctcaa ttgcacatca gctggatgag   10920
gaggagagga tgagaatggc agaaggagga gttactagtg aagattatcg cacgttttta   10980
caggtactga ttttaaactc actaagtcac atttctttt ttttttttt tttgagacgg   11040 agtctcgccc tgttgcccat gctggagtgc aatggcgcga tctcggctca ctgcaacctc   11100
tgcctcccgg gttcaagcga ttctcctgcc tcagcctccc aagtagctgg gattacaggc   11160
acacggcact atgcccggct aatttttgt atctttgtta gagatggggt ttcaccatgt   11220
tggtcaggtt ggtctcaaac tcctgacctt atgatccacc tgtcttggcc tcccaaagtg   11280
ctgggattat aggtgtgagc caccacaccc ggcttacatt tcttttaaaa atgtggatac   11340
catttagaaa aggatgggcc attcttccta tagggatctg actggtgaat tataactgtg   11400
ctgttaactt tggaaatggg aatgcacaag atattgtttt aaatatgcac gctaatgaca   11460
gtttgtatcc ttcttccc acccccaccc ttgcttcaac tacctgtcaa aattaacagc   11520
agccttctgg aaatatggat gacagtggtt ttttctctat tcaggtaagt agtcacaagc   11580
atgtactatg tgttgcttac atcccaggca ccgtttcaca gcctttcaat agtcactgta   11640
acaaggcgac cttcggaagt tcttctgtct acagagtata gattatactc tagagtacta   11700 gattttttt ttcttgagac agagtctcgt tctgtcacct aggctggagt gcagtggcgt   11760
gatcttggct cactgtagcc tctgcctccc gggttcaagc gatcctcctg cctcagcctc   11820
ccaagtagct gggattacag gcacccgcca ccacaccagt taatatttgt attttagta   11880 gagatagtgg ggtttcaccg tgttggccag tctggtctcc aactcctgac ctcagcctcc   11940
caaagtgctg ggattacagg tgtgagccac tgcacctggc caactagagt actagatttt   12000
tatatagata aacatgaaag gattgtagaa tcttcatatt agagtggggc atttaaaaat   12060
tccttcttga gaaagattaa tttgcatctg gatgctaata ataaccttaa ttctggccgg   12120
gcgcggtggc tcacacctgt aatcccagca ctttgggga gccgaggtgg gcggatcacg   12180
aggtcaggag attgagacca tcctggctaa catggtgaaa ccccgtctct actaaaaata   12240
caaaaattag ctgggacgtgg tgacacgtgc ctgtaatccc agctactcgg gaggctgagg   12300
caggagaatc gcttgaacca gggagtcgta ggttgcagtg agccaagatc gcgccactgc   12360
actctagcct ggtgacagag cgagactcca tctcaaagaa aaaagaaat ccttaattct   12420 aataagtcac aatgtctcaa acttaccatc tgttgggtaa atttgagaaa atgcaatacc   12480
ttgctaccat cctttaaat cagcctacca gactggattt ccttattatg gtttgtggct   12540
tttgattttt tttttttaat gtatagctct ctttgaattc tttggtggtt atatatat   12600 gtactcgcaa gattcttta tctgtgggtc tttcattctt tttctaacac tgtgagttgt   12660
```

```
atccagagta ctttcggaac ctctcctgag cgacctatct ctgcagatat ctttgtttat   12720
gtttcccttg tactgccctc ctggactctt cctcatccac cagcatttcc atctagtgct   12780
ttaccgtgcc actgctaaca ggtaatggct actgcagggc tgaaatcaga ggccagagta   12840
ggcccagcac ttggcgtttc ctatttgtgc cttgctgctc ttggtgcctg ttcatgtgtg   12900
cccactacct tgcactcaat ttctgtcttt gctggtacct ggctcacttg cttctttgtt   12960
ggctaccttg gagggcagat agtgaatttt cagaaatttc ccttttttg tcagacagat    13020 tgaaataaac aggtttgcat tttgtttttt ctacaagcgg caagcccatg accctagaag   13080
tctgacatct atggaacctt cagtttaaat gcccagggag aacttatttt ggtagatatg   13140
atttctgaca ttgcaggtag caagttgaat ataattttc taaagtagca cccacagcag    13200
ccaaattatc agatgtatat agtagactag ttttaagaaa agcacttatg ggtagaatat   13260
acatctggat ttttgaggca gttttatta ggaattgtgt ggttttctgg aacatctcag    13320
agacctggta tgaaaagcac tcttctaata tatatgtgtt tttttttatg gatttagtga   13380
tatatctata cacacacact ttttaaaacc tatagccggc tgggcgtggt ggctcatgcc   13440
tgtaatccca gtactttggg aggcccaggc gggtggatca caaggtcagg agattgagac   13500
cagcctggcc aacaaggtga aaccctgtct ctactaaaaa tacaaaaata gctgggtgtg   13560
gtggcgtgtg cttgtaatcc cagctactcg ggagcctcag gaggagaatc gcttgaacct   13620
gggaggcgga ggttgcagcg agccgagatc gtgccactat actccagcct gggcgacaga   13680
gcaagactct gtcacaaaaa aaaaaaaaaa aacctatagc cttctagaga aatttatata   13740
tgaagtacac aactaacata gctacacttc ctaaatttgg aatggagtgg tttagcttat   13800
gaaaagttgc tattttctt aacaggttat aagcaatgcc ttgaaagttt ggggtttaga    13860
actaatcctg ttcaacagtc cagagtatca gaggctcagg atcgatccta tgtaagattc   13920
tgttttgcat ttcatacatt tcttttccca aatttgattt ttaaagttgt aatttcttaa   13980
agaagagaaa tacattttga atacttttgt tttgatgttc cctgtttcat tcactcagac   14040 tttcctatt caccttgtg atgtccatga gcatctgccc tgtagccttc ctggcacccc    14100
agtgtctgtg gcagcacaga gctgaccccca taagtggtgc atgaggccat cttgtggcac    14160
agcatcacta agctgctgca gagacgttca tatggttgtg tgatctttta aaaacatcag   14220
tgacacttaa ctataaatat aatcttaaat tatcacaaat tttatataat atttgccagt   14280
agacaacata aatatgaatt caatatttca agttaatatt gtctgttttc ttttttagaa   14340
atgaaagatc atttatatgc aattataagg aacactggtt tacagttaga aaattaggaa   14400
aacaggtaac atttcttacc cttccttgtc tttttttctt atattgtacc ccatttaaaa   14460
ctaaaatgtg ggccaggtgt ggtggctcat gccaacagtt tgggaggctg aggtgggggg   14520
atcacttgaa gccaggagtt tgagaccagc ctgggcaaca agggaggtc ctgtctctta    14580 aaaaaaaaat aaaaataaaa ataaaaataa ataaaaaaaa aaacaaagag ccaggcatgg   14640
tggctcacat ctgtaattcc agcttacttg gaaggctgag tcagaaggat cacttgagct   14700
caggagtttg aggctgcagt gaactatgat tttgtcactg taccccagcc tgggtgacag   14760
agtaagactg ttctataaaa cataaaaata aaaaaatat atttaaaaat taaaaaaaaa     14820
aaaggattgc tgactttaaa attaggaaac tgaccagtaa tgtgtgtgtg tgtagcatgg   14880
tttatccttc ttgatagata gaaattgtca ttttaaaaga taatatcagt tttccttata   14940
aatttatttg tgacaagtat atgcaattta actatatcat aagaaaaatt ctatattaaa   15000
gataatacaa atgtggttac ttttaagtgg gttttatgt gatgactatg ttctgtcagt     15060
```

```
taattattac atttatagat ttgtatttag catagtgctg tcacaaagcc tgaaatagtg   15120
tcaagcatga ataaagcatt caattatgtt tgcttagtg taagattatt cattatgatt   15180
ccaaaagcca tgtaatacgt acgtctacag aaaatcactt ctatttttta aataaaacat   15240
gaaatatgtc ttgagcaagc tattttaaga aacaatcatt taacgtcctt gttattagaa   15300
ttttgaatct ttgaaagagg gttattgaaa accagctagg acagtaaaaa agaataaact   15360
agtgatacat gcagcaatat ggatgaatct caaaataatt atgctgaaag aataacccac   15420
aaacaaaata ctacctgctg tatggtatca tttattaaaa gtctagaaaa gtgcagattc   15480
atctgtagtg atggaaagca gattgaccag cggttgcctg gggacgagaa ggctatgag   15540 gagtgagagg ggagggttac agagaggcac gggaaacatg gcaatgagga atgtgttcac   15600
tatcttggtt gtagtaatgg tttcatggga gtacagtata caaatgtgaa acatttcag   15660 aggccagatg cagtggctca tgcctgtaat cccagcactt ttggaggcca aggcaggagg   15720
attgcttgag ctcaaggagt tcaggaccag cctgggcaat ggcacaagac cccatctcta   15780
aaaaaaaaat gaaagaaaaa aaaattggct aggcgtggtg atgcatggcc gtagtcccag   15840
gtgctaggga ggctgaggag ggagcacaga ggtcaagcct gcagtgaatc atgatcgtgc   15900
tactgcactc cagcttgggt gacagaagga gatcctgtct caaaaaaaaa gtttcaaatt   15960 atacactta aatatgtgca gtttattata tgtcacttat accccaataa atctgttttt   16020
tttaaaatgt aaatacaagc caaaaaggt ataagtcaag aaaatatatt gaattaaatc   16080
tgtaagagat aattcaaaaa caaaacct attgttatct tttaagtcac ccaaatcaaa   16140
tttgggaaaa gtcacctact tagcttcatc ctaagttggt tctttctttc tttctttcct   16200
tcttttgaga cggattcttg ctctatcgcc caggctggat tgcagtggcg ggatcttggc   16260
tccctgcaac ctccgccacc tgggttcaag caattctctt gtctcagcct cccaaatagc   16320
tgtgtctaca gccacgcacc accacaccca gctaatttt gtattttag tagagacggg   16380 gtttcgccat gttggtcagg ctggtcttga actcctgacc tcaggtgatc cgtccgtctc   16440
tgcctctcaa agtgctgggg ttacaggcgt gagccaccat gccgagccct aagttggttc   16500
tttcttaaag ttcttcctga ggagccaaga gcaagttaag gagatgtaac ctagaagctt   16560
acagtggagg ctagctgggt gcagtggttc acgcctgtaa tcccagcact ttaggaggct   16620
gaggcaggga gatcactgag gccaggagct tgagagcagc ttggcccaac acagtgacac   16680
cttgtctcta caaaaaaaa aaaaaaaaa ggcagcttac agcagtagag gctgatgcga   16740
gtgggaatca cctctaggta aaaaccagtg tagcgtactg ctgagattat ttaacctctg   16800 ggttttatt atgtgttttt aaaaattatg atccagtatt ttttactttt ttttgtataa   16860
agtaagcact gaattttaa ggttgtatta atttgcaaat aaatgtctat cttattttt   16920 tgagagattt aaaaaatttt agttcttcaa aattgcattt tcacattttg aattacgtta   16980
tctttgacaa atacagaaga tgtcaaattt tggtttattt tctttggttc taatttatat   17040
ttttgtttaa aactatattt ttcactatag actctttctg tctctcgagg tccctgtata   17100 atgaaaaga aggctggaaa aagtattaac attgtcaaaa tccaggaaaa gtagttggtc   17160
atgatattga tcgttaactt tagaaacttt ttgtatcttg tgggttaaat taggattact   17220
atgtggtagt gataaatgat gttaattagg gccgagtgca gtggctaaca cctgtaattc   17280
cagcatgtag ggaggctgag gtgggaggat gtcttgaatc caggagtttg agaccagcct   17340
gtacaacata gtgtaagacc ccttctccac acaaaaaaat tagaaaattt gtcaagcatc   17400
```

-continued

```
ttggtgcaca cctgtagtcc cagctgcttg ggaggatgaa gcgagagaat cacttaagcc    17460
caggtgttcg aggctgcagt gagctatgat tgcaccactg cactccagac tagatgacca    17520
tctcttttaa aaaatgtgt ttatatgtta tatgtgatag tgcttttta aaacatttt      17580 aaattataga gacagggtct cactatgtta cagcccaggc tggtctcaaa ttcctgggct    17640
caagcaatcc tcccacctta gctaacctcc caaagtgctc ggattatagg catgagctgc    17700
atgcccagct aatttagtga ttttttaaaaa ctgagctggt aattataaat tctcttcctg   17760
gaacttctga ctttctcaca attggaatct tttgacaaaa attatcagta atgggaaaac    17820
tttgtgtagt tgtcattttt cctcccatca gtgtgataga tatgattgga gttatgttgg    17880
actgatattt tgaaaaaaga tttaattata gctattaata aagacattta aactactgac    17940
tatgcatttt tattcttttg ggagggttta atgtttatag tttaaagcaa actgttgttt    18000 ttaaaaagt atctaacagg gccgggcgcg gtggctcaca cctgtaatcc cagcactttg     18060
ggaggcctag gcgggcggat cacaaggtca agagatcaag accatcctgg ctaacatggt    18120
gaaaccctgt ctctactaaa aatacaaaaa atagctgggg tgtggcggcg tgcgcctgta    18180
gtcccagcta ctcgggaggc tgaggcagga ggatggcatg aacccgggag gcggagcttg    18240
cagtgagccg agatcgcgcc actgcactcc agcctgggcg acagagcaat actctgtcta    18300
aaaaaaaaaa aaaaaaaaaa aaaagagtat ttagcagagg ccaggtgcag tggctcatgt    18360
ttgtaatccc agactttggg gaggctgagg cgggcggatc atttgaggtc aggagtttga    18420
gaccagcctg gccaatgtgg caaatgtgct gtctctaact aaaaatacaa aaattagctg    18480
ggtgtggtgg tgcagacctg tagtcccagc tacttgggag gctgaggcag gagaatcact    18540
tgaacctggg aggcagaggt tgcagtgatc cgagatcatg ccactgcact ccagcctggg    18600
ttacagagtg agactcttct caaaaaaaaa aaaagtatt taatagtgat aaatctgcag     18660
tattctcttg tagtttttaa gatcatatta ttcagtcaaa gaaagagct caacttgaaa     18720 tatttccaga gtttaaacaa tcttactaag ctttgatggg ttgtatctat tcttaacatg    18780
tgaaacttcc ttattaccta taatatacac taacttaaat attgacaatt ttttccagt    18840 ggtttaactt gaattctctc ttgacgggtc cagaattaat atcagataca tatcttgcac    18900
ttttcttggc tcaattacaa caggaaggta agtaacggct gaacattttg taatgttacc    18960
tttcgaagta gttaaataac caggcacatt agatgacagt gtgataaaac tgttttttctg   19020 gcagtggcag tgaaacaatc tttagttttg acgtggtgat aggctgtgat ttgggtgacg    19080
ctgttcagtt agagttctca ctgacacctg gcccttcctc ttctgaggat gctgctttct    19140
ttgcagccct tctaagtaat ggcttttttct tttatacatc acatatcaca cggctgagag    19200
gagggataga tgttttttctt ctttgcctct tctaggccac tgttcttcct tataaactcc    19260
agtttctttg aaatacatgc ccctaacggc tgggcacggt ggctcacgcc tgtaatccca    19320
gcactttggg aggctgaggc aggcggatca cgatgtcagg agatcgagac catcctggct    19380
aacacggtga atcctgtctc tactaaaaaa taacaaaaaa ttagccgggg tgtggtggcg    19440
gacgcctgta gtccgagcta ctcgggaggc tgaggcagga gaatggcgtg aacccaggag    19500
gcggagcttg cagtgagctg agatcgcgcc actgccctcc agcctgggcg acagagcgag    19560
actccgtctc aaaaaaaaaa agaaaagaaa aaaaaagaa atacatgccc ctagattaaa     19620
ctatcccttg tccttttgca ctcatccaca agtctctttt catcagtgat tttaggatct    19680
gactcgttgt cttttctct acttcaacta cttttatcat tcttaattat ttctgtatcg    19740
tcaatcaatc cagtacctgc ctcttagttt caaaatcact tactcttgct tagctattac    19800
```

```
cagtaatcat aaccactgtc aaatctcaat tgcaagcata ttactcttta actaccacct   19860
cctatcttta aaccatgttt tgtctgtttt tttattccag ccattcttta aaccctactg   19920
tggggcccaa gcatttcctt tatacgcatt cttcctttct tctactgctt attttctgta   19980
atccgtcatc ataatcactc cattgcattc ttcaacgtgt ttcccctctc tccctccatc   20040
atacttgaat gacaaaaatc tcaaccctgg ttaaaccaca tcttggcctt gtccattcct   20100
gtaccagagt agctggacgt ggctaaaaaa taacataaaa catgatgatt ggttttactt   20160 tttcttaaa tgatctatcc atccattcac ccatccatct atcaaagtga ctaggcctat    20220
ttctgaagcc caggctggag tgcagcagca taatcacagc tcattgcagc tccaaactcc   20280
tgggctcaag tgattctctt gccttagcct gttgagtagc tgggactaca ggcttgtgct   20340
accacaccta gctaaggttt tactttaaat ttattataat cacaaaattc agatgagcct   20400
ttagtgctgt ctgatatttc tactatgttt tcttagtgat gtaccaccct ccaaggtgtt   20460 tataaaaat tatgtaccac tctccaagaa gtttataaaa aataatgtgc caccctccaa    20520
ggtgactaat ttcacagctt atgtctttaa acctttaagc actttcctct cccttacaca   20580
ccttccttgt ggctttccgt tacattctgc tgagaacata gaagcaatta aaattatgtt   20640 cttctacca gcaaatttat caatttgctt atatcttcac ctgtgctttg agcctattta    20700
aatagatgaa tggtcccctta cctctaacca aaaccagtcc ctcacttgtg ggctggatcc   20760
cagctcttct cacctactca agatgttcct gctttcatct ctccactctc ttatataatc   20820
agttcccccc cccttttttt gtaatattcc tataagcagt aaaataagct ttttatttcc   20880
attgattaaa aataaaaatc ctctcttaat tccatgaaac tccagctgcc tccccatttt   20940 tatttttcc ttaggattgt ctctagtgtg ccttctcctt ttcttgaact ctgcctcctg    21000
ggttcaagcg attctcctgc ctcaacctcc cgagtagctg ggattacagg cgtgcaccac   21060
catgaccggc taatttttt tttttttttt tgagatggag tttccctctt gttgctccgg    21120
ctggagtgca atggcgtgat ctcggctcac cgtaacttct gcctcctggg ttcaagcgat   21180
tttcttgcct cagcctcccg agtagctgga tttacaggca tgtgccacca tgcctggcta   21240
attttgtatt ttagtagaga tggaagggggt ttctccatgt tgttaggct ggtctccaac    21300 tcctgacctc aggtgagccg cccacctcgg cccctaaag tgctgggatt acaggcatga    21360
gccactgcgc ctggccccgg ctaaattttt tttttttttt tttgtatttt tagtagagac   21420
agggtttcac catattggcc aggttggtct cgaattcctg gcctcgagtg atccacctgc   21480
ctcagcctcc caaagtgctg ggattacagg cgtgagtcac cttgcctagc catcttttag   21540
taatggtatt tggagatcac aatttgagtg ctggcatgct tattgctgct gggtttgtta   21600
tgtagttatt gtgaattcac atttaggaat atagggtttt taattcttg attttagata    21660 cttgtatctt ttttctttta tatttaaaac cttggttcct gatgatatcc cttcttagaa   21720
accctgtcta cctttggcct tcagcccacc atgctgtggt tttcctaact tgctgcctgc   21780
acttttcaga ttcctttcat ggatcttaaa tatcatctgt aaataagatc tatgtgtcaa   21840
taattaccaa acttttatct ttagtcttga catctaccct gaacacctag ctttgactaa   21900
ctcctagctt tggcatctcc acttggaaat ccaaaaagtg tttcaaactg aacatgtcta   21960
tgaaagactt atttttttct ctctatccat gctatccatc aggttttcca tttccataag   22020
ggtgactctt gtactctggt tcctatatat tataccgaca gagcagccca gagtgcttct   22080
taaccagtgt aaggcctgtt atgtcccacc ctcactcttt gtccttcagt ggcttcccag   22140
```

```
cacacttaga ataaaatctg aagtcttagg ccgggcttgg tggctcatgc ctgcaatccc   22200
agcactttgg gaggatgagg gggcagatca cttgaggtca ggagttgatg agaccagcct   22260
ggccaacatg gtgaaaccct gtctctacca aaaatacaa aaattaactg ggtgtggtgt    22320
tgtgcacctg tagtcccagc tactcgggag gctgagatag gagaatcact tgaacccggg   22380
aggcagaggt tacagcgagc caagatcata ccactgcact ccagcctggg tgacagaacg   22440
agactctcaa aaaaaatta aaaaaaaaaa atatgtgaag tcttgaataa acccaagat     22500 ctttaccatg gccctgaac agggcagagt atccattctt cagacactct tcatagaata    22560
ccatggtgag ctggcatatt tattatacaa tacagaaaca attttactgg cagaaaacac   22620
attaaaccgt ctaaactctg aatacagttg tcctcataaa aaatgttcaa catactattt   22680
tgaggttttc cattaatagt tcttataatc tttgtcccat tatgtgttaa tccaacaaag   22740
gatatccaat aacaaacacc aaagtttaag aaaaatgtgc taggcgcggt ggctcacacc   22800
tgtaatccca gcactttggg aggccgaggt gggcagatca cctgaggtca ggagttcgag   22860
accagcccag ccaacatggt gaaaccctgc tctcctaaa aatacaaaca ttaactgggt    22920
gtggtggtgg gtgcctgtaa tcccagctac tcaggaggct gaggcaggag aatcgcttga   22980
acctcctggg aggcagaggt tgcagtgagc taatattgca ccactgcact ccagcctggg   23040
tgacagagtg agactccatc tcaaattaaa aaaaaaaaa aattaatgat agagaaactt    23100 aaaatcagtta gattgttta ggtatagccc atccttggtt tttgtgtgta gcatctagct   23160
tggggaaacc ctggatttct ggaatcatat ttagacacag tcacactaga ctaatgtaat   23220
tcttttggga tgcaaaccac acgtttgaca ccttaaatag cttttaggta tttggcttcc   23280
cagcccctat ttttagttac aaggggtgta catgtgtggg tcagggtggg ggtagctctt   23340
tccgcagatg attagtttta gccatgttac tagttattgc acacattatc tgtgtcctca   23400
cagcagccct gtgagtaagt gtattagggt tctctagagg gacagaacta ataaggtaga   23460
tgtatatatg aagggtaatg tattaaggag tatcgactcg tatgatcaca aggtgaagtc   23520
ccacaatagg ctctctgcag gctgaggaac caggaagcca gtccaagtcc caaaacctca   23580
aaagtaggga agctgacagt gcagccttca gtctgtggca aaaggcctga gagcccctgg   23640
caaaccactg gtgtaagttc aagagtccaa aagatgaaga acttggagtc tgatgtttga   23700
gggcaggaag catccagcat gggagaaaga tgaaggctca gcaagtctag tacttccaca   23760
ctcttatttc tgcctgcttt attctagctg agctggcagc tgattagatg gtgaccaccc   23820
agtttgaggg tgggtctacc tctcccagtt cactggctta aatgttaatc tccttttggca  23880 acaccctcgc agacacaccc agaaacaata atttgtagcc ttcaatccaa tcaagttgat   23940
aatattaacc atcacaggaa ggtactagta tcatatgttt aacagtagaa accaagacaa   24000
atgcagctag gaagtgggag aactgggatc agatgcaggc agtctgattc taaatcagtt   24060
gctgttaccc actctgacaa cagtaagtga gtagcctgct cagtcaagta ctatattagt   24120
agggcccttt acagacatat ttatttctca cagtcactca atgagacggc tcttccagtc   24180
ttacaatgga gaaagtgagg ctcagagact ttaagtaact taccttagac gactttacta   24240
gtaagtataa gaatcattat ttggactaaa gtctttctga atcctcagct tgtatttttt   24300
tccagtgttc tgtgctgcct ttttatctac tagtgtttta catcaatttt gaatctcttt   24360
actaactggt taggttgatt tttgcctttt tttttaggt tattctatat ttgtcgttaa    24420
gggtgatctg ccagattgcg aagctgacca actcctgcag atgattaggg tccaacagat   24480
gcatcgacca aaacttattg gagaagaatt agcacaacta aaagagcaaa ggtaaaaatg   24540
```

```
aggcctgcag tatggaatat atggtagtat ttcattatga gaattaaatt ttcatgctta   24600
gattgaatat gtggtccttg tgttgttggc gactctattt tggaccttat attttagtga   24660
agtttattag tttaaacttg aatcaactct ttgaaatact taaatatatt aacttagtta   24720
gctggtatgg tatattccta gcacttcggg aggctgaggc aggctgattg cttcaaccca   24780
ggagttcgag accagcctgg gcaacatggc aaaacctcat ctctacaaat agtacaaaaa   24840
ttagccagat gtggtggtgt atgcctatag tcccagctac ttgggaggca gaggaagaag   24900
gatcacctga aactggggag gtagagacta cagtgagcca taatcacact accgcactcc   24960
agcctggtcg agagagtcag accctgtctc aaaaaaaaaa aaaaaagaa acggaaaaaa   25020 aaaacttagt tggattcaaa ttgcaacaca atcattatat tactagagct tatttgccag   25080
aaaacatttt aagttttgac ttacttaaag cctttacatt acaaatgcct ttatgttatg   25140
tctaaaatag aagattggtt gcagttatta ccagtgcttt tgttctttag agtccataaa   25200
acagacctgg aacgagtgtt agaagcaaat gatggctcag gaatgttaga cgaagatgag   25260
gaggatttgc agagggctct ggcactaagt cgccaagaaa ttgacatgga agatgaggaa   25320
gcagatctcc gcagggctat tcagctaagt atgcaaggta aagacattct gatgtgtgtt   25380
gtattcattg ctgaagaatt gattccaatt attcttagat ttcatggaag ttaatgtact   25440
cttagaggtg ttttgacaat tactgcagaa gcaatagcta tatagtgggc tttcccttta   25500
gatttcttat aatggaaatc acttttaca acctatattt tattaggagt agttatattt   25560
ttactcctgg ttattttatt tggtttcaac actgtactaa cacaatagta aattgtggtt   25620
ttaatctttg tgggtatcag ttgacccctta tccaaatcag ctgttacata aatatgtgcc   25680
attagacact atggaagggc ctggacaggg aatataaact gattttacaa aaacccaaca   25740
tttattggct atgcaactta aaccgtaagc ccactttggt gggcccagtt ttttagtgat   25800
ataaactatc aatagagaaa agcgaaaaca tatcccctag acaatctagg caaagaaaaa   25860
tgttaagaca tagctcaaag tagcttaatt aaaagtttga agtgggtttt ttgttttatt   25920
tttttctaac tcatatgtat ttgcttctac tttctaatga aattatttat cagttgattt   25980
ccttagatat ctaaataaaa ttgaaatttc attaatggga agattatttt tatcctgaac   26040
ttttcttgcc tctatgcatg cctctgagta ctccatatgg tgtgcaatcc cattttgat   26100 taatagagtc ctgctggatt agcagggaca gaaatcagct ttagatttct ttcttttttt   26160
tttttctttc tttttttttt ttttttttt tgagtcagag tctcactgtc gcccagcctg   26220
gagtgcagtg atcttggctc actgcaaccc ctgcctccga ggttcaagcg attctcctgc   26280
ctcagcctcc tgagtagctg ggactacagg cgcctaccac cacgcccagc taatttttg   26340 tacttttagt agagataggg ttttgcccctt tggccaggc tggtcttgaa ctcctgacct   26400
caggtgatcc acctgccttg gcctcccaaa gtgctgggat tacatgtgtg agccaccacg   26460
cccagccaga agagtagaat attcttaaag agaaaacgtt ttaaaggctt actcaaatga   26520
gtataaacaa acatattgtt gcttgaattg gtaaatacag tgattggttt ttgttgtgtt   26580
gtgttttgtt ttcaggtagt tccagaaaca tatctcaaga tatgacacag acatcaggta   26640
caaatcttac ttcagaagag cttcggaaga gacgagaagc ctactttgaa aagtaaagta   26700
gttggtacaa gttaaagtag catgtttaat atttgctttg gctattttgt ctatttgtaa   26760
atggttactg cctgaatcct gtgaatattt gaatgtattt tttaaaaatt tacagcaaat   26820
aggacgggca cggtggctta cgcctgtgat gctagcagtt tgggaggcca aggcgggcag   26880
```

```
attgcctgag gtcaggagtt cgagaccagc ctgggcaaca cagtgaaacc ccatctctac   26940
taaaaataca aaagaatcag ctgggcatgg aagcgtgcgc ctgtagtccc agctgcttgg   27000
gaggctgagc caggagaatt gcttgaaccc gggacgtgga ggttgcagtg agccgagatc   27060
gcaccactgc cctccagact gggtgacaga gtgagactcc gtctccaaaa atatatgtat   27120
atatatataa ataaaaataa aaatttacgg caaataacat gaaacaaaaa aaccttgccc   27180
caatactgga taaattttt aaactgagtg aaggaaacct tataaaattt catttattaa    27240
aagaaaaatg aaattaggac aagacaagaa gaatgccaat tgatcctttg gatgtacttc   27300
ttgcttacct gattaaccct gcaaaattcc tctaccaatc agtacgaaaa acagctttgg   27360
aggtatggga gcgcattccc aaatagacgt ggtagttcat ttagctgctc atggccgctt   27420
caggcagtcc tgtaagcctg ttagcatcag gggaatggat gcaaaccata aatctggatc   27480
aactcctaaa accttacctt gtgcccagcc ttgtaagtgc ttgctaaata ggaattccac   27540
catatgaaaa tacattcttt tcaagtaact atcattcaga cttttgtccc ccacttttt    27600 ttttaaaga aaaataaaag gctgggcacg gtggcttacg tctgtaatcc caccatttta    27660
ggaggccaag gcaggtggat cacctgaggt caggaattca agaccagcct gaccaacatg   27720
gtgaaacctc atctctacta aaaatacaaa aattagccgg gcatggtggt gggtgcctgt   27780
aatcccagct acttgggagg ctcagacagg agaatcgctt gaatctggga ggcagaagtt   27840
gcagtgagct gagataacgc cattgcactc cagcctgggg acaagagcg agacttcgtc    27900 tcaaaaaaa agagaaagaa aacttcatgt taaagattac aagataaata atcagaccca    27960
ctgatcctag gtcagaaaac agagtcatag ctcaatctga cttactattt gctgtatttc   28020
atccattctg agatgcacat agtttcacat ttcaatgtct ctgaaattga gaagcatctt   28080
acagtcataa ttgacagtat attagcagca cctataaata ttggctcatt ttacatttga   28140
tggtataatg aagaaaatat ttacctttt ttctgtttg tttttaagtc acaactcaga     28200
agtagatgaa ggaaaattct gatcagctga catcctctta atgtgagata tttctagtct   28260
ttattcagta tagattaatg gctaattata tgttaaattt caaagtagtg cttattagtg   28320 cttttact ttaagtttca aaattaactt ttttattata ataaactcca aatttataca     28380
aaagtagaaa aactagcata ctcctgttta tgacccagat tcaacaaata ctagcacacg   28440
gccaatcttg ctttttttt tttttttt tgagatggag tcttgctctg ttgcccaggc      28500
tggagtgcaa tggcacaatt tctgctcact gcaacctctg cctcctgagt tcaagcgatt   28560 ctccacttc agcctcccaa gtagctggga ttacaggtac acaccaccat gcctggctaa    28620
ttcttgtatt tttagtagac acgggatttc accatgtcgt ccaggctggc cttaaactcc   28680
tgacctcaag tgatccacct gcctcggcct cccagagtgc tgggattaca ggcatgagcc   28740
actgagcccg gcccaatctc gtttataat actcccatct cccattcttt ccactgtccc    28800
acctgcaagt ttggattatt ttgtaacaaa tctcaatcat catattattc tataaccatt   28860
ttaatatgtg tctctaaaat atattagctt tattttaac atagttaaat gctattgtca    28920
taaaataata atcataataa ttaattgtaa ttctatatca tcaattatct agttaatgta   28980
aaaaataaat ctaaggccag gcgcggtggc tcacacctgt aatcccagca ctttgggagg   29040
ctgaggtggg cagatcacct gagatcagga gttcaagacc agcctgacca catggagaa    29100 accccatctc tactaaaaat acaaaaaatt agccaggcgt ggtggcgcat gcttgtaatc   29160
ccagctactt gagaggctga ggcaggagaa tcacttgaac ccgggaggcg aggttgcggt   29220
gagccgagat cgtgccattg cactctagcc tgggcaaaaa gagtgaaact ccatctcaaa   29280
```

```
taaataaata aataaataat aaaaaataac ttaaatctac ttaattagaa aaactaacat    29340
tctaaaaatt ttattttaag aaatatcaaa attggctggg cacggtggct cacgcctcta    29400
atccctgcac tttggaaggc tgaggtgggc ggatcacctg aggtcaggag ggtcaggagt    29460
acaagaccag cctggccaac atggcgaaac cctgtctcca ctaaaaatac aaaaattagc    29520
caggcatgat gatgggcacc tgtaatccca gctactcagg aggctgagac agaagaatcg    29580
cttgaaccca ggaggtagag gttgcagtga gctgagatca ccccactgca ctccagcctg    29640
ggtgacagag tgaaactccg cctcaaaaaa aaaaaaaga gaaagaaat atagaaatta      29700 aagcatacat ggccaggcgt agtggctcat gtctgtaatc ccagcacttt gggaggctga    29760
ggcaggcaga tcacttgagg ccatgagttc aagaccaacc tggccaacat ggcgaaagcc    29820
tgtctctact aaaaatacaa aaaaattagt tgggcatggt ggtgcacacc tgtaatcaca    29880
gctactttgg aggctgaggc aggagaatcg tttgaaccca gaggtggagg ttgcagtgag    29940
ccgagattgt gccactgcac tctatcctgg gtgacagagc gagatactgt ctcaaaaaga    30000 aaaaaaaag gctgggcgcg gtagttcatg cctgcaatcc cagcactttg ggaggccgag     30060
gcaggcagat tacgaagtca ggagatggag accatcctgg ctaatacagt gaaacccccgt   30120 ctctactaaa aaatacacaa aaattagctg ggtgtggtgg caggcacctg tagtcccagc    30180
tactctggag gctgaggcag gagaatggca tgaacccggg aggtggagct tgcagtgagc    30240
agagatcaca ccactgcact ccagtctggg cgacagagcg aggctctgtc tcaaaaaaaa    30300
aaaagaaagc atactctcac ctccttcagt gactgatgtt agtattttgg cacattcttt    30360
ttctgtgaca tatacacact taccttgtaa gtgttgtact catttcctat gacagtaaat    30420
agtctttgta acaggctgca tgatatttca taaaatgaat ggatgtggca taatttatat    30480
gtgagccttt tgaattctgc tattataatt aatattgcaa tgaacaattc ttatattgcc    30540
tctacacctc aaatgtctta tcatttcttc tagttttttct gaggatgtca gattattggg    30600
ttaaaggata tgaacatttt taaggccttg aacagatttt ctaaattgct ttccagaata    30660
attcccatgt gatactttca ccatgtttat ttcagacttt ttttttttt tttttttgag     30720 acgaaatctc actctgtcac ccaggctgga gtgtagtggc atgatctcgg ctcactgcaa    30780
cctccgcctc ctgagtttaa gcgattattc tgcctcagcc tcccaagtag ctgcggttac    30840
aggcaagtgc ctccatgcct ggctaatttt tgtgtctttt gtagacatgg ggtttcacca    30900
tgttgcccag gctggtttcg aactcctgag ctcaggcaat ctgcctacct cggcctccca    30960
aagttctggg attacaggcg tgcaccaccg cgcccagcca tcagagtctt ttttgtcaaa    31020
ataaaatggt ctaaagacat acatcataga gaaactataa tacaaaattt acaggtatat    31080
ctaagaaaag aaaagtatat ttaaagcata aaaataaact gctctttttac ttaaaatttt   31140 ttaaaaactg gattaaaaat atgaaacttc caacaaattg agcttttttt tttttttttt   31200 tctttttga gacgaggtct cgcttttgtc acccagtctg gagtgcagtg gcgcgatctc     31260
ggctcactgc aacctccacc tccctggttc aagcaattcc cctgcctcag cctcccaagt    31320
agctgggatt acaggcgcat gccaccacgt cgggctaatt tttttgtatt tttagtagag    31380
agggggtttc accatgttgg ccagactggt ctcgaactcc tgatctcagg caatctgcca    31440
gcctgggtct cccaacatgc tgggattaca ggcatgagcc actgcactcg gcctgaactt    31500
tttatagtag taacgataat tcagtaatgt ccaataatga ctaagtaagt tataacaagt    31560
acaatgtcag caataactag tgcttttttag taaacagggt caggcaacct tgtacccttt    31620
```

```
taaaaatgtt cgaatatcga tatacctcct tcctacttgg tggaggattg attgaggagg    31680
aaagtgtgca gtgatggtta ccagcttcag cctcttggct tgactttgca aatactggtg    31740
agaatttgga aagagcttga gaatatctta catagtcaca tgttgctgag aagagttaag    31800
aactaacttc ttgatgttca ttttttaacaa tggcttgcat tcaaaacctt gtagagctca    31860
ttagtaggag ctaagaagct aatatttgcc tttcactaaa attcctgatt acttagccta    31920
ggtagttcgt tgtctctcta ggttctgtct tgggagcttg ggtctaagg ttatcaagct    31980
aactctttct tccctctcac ccttcccaaa ttgaccctgg tgctgatttg ttattcatac    32040
gattttctag ttttttctttt cccttttttga gtatttgaag cttcatactg aatatagtaa    32100
tcatagtatt catgcataaa gaaaatcata aagtaattgc ataaatgcat aaagtaatca    32160
tagttttcat gcattaaaaa aactagtttt ggctgggcgc tatggctcac gcttgtaatc    32220
ccagcacttt cggaggccaa ggcaggcgaa tcatctgagg tcaggagttc gagactagcc    32280
tggccaacat ggcgaaacct cttctctact aaaaatacaa aaaattagc cgagtatggt    32340
ggcgggcgcc tgtaatccta gctatttggc aggctgaggc aggagaatca cttgaacctg    32400
ggaggcagag gttgcagtga gccgaggttg tgccattgca ctacagccta ggcgacaaga    32460
gcaagactcc atctcaaaaa aaaaaaaaa aaaaaaaaa ctccctatta cagattcata    32520
atttatgagt cattaaataa tattttcaag ccatgacatt ttttccagca gtagtctcta    32580
aatctgtttt accatcataa aaccccaagc aaaactctac tacatcagct gtgtcactgt    32640
aaaacctgcc ttaactcaca gaagcatgaa attaagcaat gtgtgtgaaa ctattttata    32700
aactgtaaag tattccatac atacatgttg gcagttatta atgtcttctc taggtgtggc    32760
tttgaaatgg atgcagatgc tttctgttac aaaaaacata agttgcaaat gttctataac    32820
aaggagagac acaaatatct tcatggacat ggattgctat gagtgtttga ttgcctaata    32880
cttgagccac cacttcagtg atatggtata atttatcaaa cagtgttgag aaacagaaac    32940
tactggggat gttttaaaga ggaaaatact taatatagaa attaggggtt tacataatct    33000
taagaaagga tgaaggtgca gctcttagcc aggcctccac agtaccacaa accaacttgc    33060
aggaagagct gtaaccactg ccccagttgg gacaatgggt aatgaggata ttaaatttaa    33120
gaacatactg ctatagcaat gatccttggc atagaaagct gccaccacaa ttgcctagag    33180
atgggaacat gaagtctggc ccccattgca acagcagtga agcagaattt tgggactggc    33240
atctcccaaa tggctttgct tgccaccaga gaacaaccaa agtggaggga gatggctagg    33300
cctcatttct gcctatttta ttttattttt tgagacggag tcttgtctgt cgcccaggct    33360
ggagtgcagt agtgtgatct cggctcactg cagcctccgc ctcccagctt caaacaattc    33420
tcctgcctca gcctcctgag tagctgggat tacaggcacc cgccactgtg cccagccaat    33480
tttcttattt ttagtagagg tggggttttg ccacgttggc caggctggtc ttgaactcct    33540
gacctcaggt gatctgcccg cctcagcctc ccaaagtgtt gtgattacag gtatgagcca    33600
ccatgcctgg cccatttctc cctttttttt ttttttttt ttttgaggtg gagtctcact    33660
ctgttgccca gactggagtg cagtggtgca atcttggcgc attgcaacct ctgcctccca    33720
gtttcaagca attcttctgc ttcagcctcc tgagtagctg ggactacagg tgtgtagcac    33780
cacacctggc taattttttgt ttttgttttg ttttttttga cagagtctc cactctgtca    33840
cccaggctgg agtgtagtgg catgatctgg gctcactaca acctcgcct cccgggttca    33900
agcaattctc ctgcctcagc ctccagagta gctgggatta caggtgtgcg ccaacacacc    33960
tggctaattt ttttgtattt ttaatagaga tggggtttca ccatgttggc caggctggtc    34020
```

```
tcgaactcct gacctcgtga tccgcccgcc tcggcctccc aaagtgctgg gattacaggc    34080
atgagccacc gtgcccagac aaggtttgta ttttagtag agacagtttt gccatgttgg     34140
ccaggctggt cttgaactcc tcacctcagg tgatccgcct gccttggcct cccaaagtgc    34200
tgggattaca ggcgcaagcc actgtgcctg acccgtttct gcttttaaa gctcatgtga     34260 gcacttaatt tgtaaccaga atcctacttg taaaataatc taagacatgt agcttttagc    34320
tttgtaacct ctataatatt gatggcacag tgggagtgga tgctgagtac cacttgaaca    34380
tgttccacct cagtgtcttc acagctggaa ggtgtctaca ttgtttcaag gtggacaatt    34440
gatttacttc tcattttca taaactaaaa gtagaataaa ggctattcct ctaaaattgc     34500
tatctcacct gtcactccct tgcattctca catacccttct tgagtggagg ggcagagggc   34560
atggagtgat agcagatgtg ccaggaattc tccataactc agtccgtccc tcttgtgcta    34620
tgttgcagca tcaggatttg ctaatgggag gatactgccc ttacgtgcat cattagccat    34680
gcacactaag gtcttacacc tacacacagg tcagtattct ggctcagaga ccaacaggga    34740
gaaattgcag ttctcattag ttgaactttc tttattgttc acagttttaa aacacaaaat    34800
tgagaggaac tctataaaa atgtgccatt ctattaataa ttgttgctgg taatttaaaa     34860
atccttgttc ctttcaaat tcttatatac cttttttttt taaacacttg atcttagcca     34920
aaagaccgag aagcaatctt tttttttt ttttttttt ttaacctata gcttctcact        34980
gagattgtca gctgtttgta agtttggtt tttggttttc tgtgtttgta tttacatata    35040
tgaaatacag attgagtatc ccttatccaa aatgcttaag actggaagtg ttttagattt    35100 ggggttttt aggatttgtg aatatttgca ctatacttac cagttaagca ttccaaatcc     35160
aaaatttcaa atctgaagtg ttccactgag cacctctttt gagtatcatg ttggtgctca    35220
aaaagtttct gattttggag catttggatt tctgattctc ggatttagga tgcttgacct    35280
gtaatttcag atttacataa aagcagaaat agtacacaga gctccttata tccttcaccc    35340
agattcccca attattggcc tttctgaacc atttgggaat aatatgcaga tatgattttc    35400
cattatgtct cagttgttca gtgtatattt tctaagtaca agaatatatt cctacatatt    35460
tacatgataa ccgtcatgtt taaacatttt aaaatgggga tttgtattac attgtttctc    35520
tttttgaaaa aattacagag gagcttaatg caatcagtat tacttaaaat ctgataatgt    35580
gtgttaaata gtagttttca tttatttcat ttatcaggtg ttcagtgaat gcttactatg    35640
taacagcaca gttatcagca ctggggaaat agatgagtaa gataagattt gcactttcat    35700
tagcttacat gccataaaga gggaaataaa gagaacacca gatgatgata agtttatgct    35760
gagaattaaa atgaagtgat gaaataatgg gaatgtcagg tggctacttt tggtgggatg    35820
gtcaggaaag gcatctctgg ggagataaat tttaagctca gacctgagtg aaaagaatga    35880
gccagccatg gaaacattat gttaactcac atggtagttt gaaatgcttt atctgatcaa    35940
aggtacttat ttttggtgac tttcaacaat attaagggtc tataaaccaa cactcatttg    36000
cataagaata actaccagtg aatcttttg tatgataggt tttttgtttg ttgttttttt     36060
gagacagagt ctcgctctgt cgcccaggct ggagtgcagt ggcgcgatct tggctcactg    36120
caacctctac ctccccggtt caagtgattc tcctgcctca gcctcccaaa gtagctggga    36180
ttacaggtgc ctgccaccac gcctggctaa ttttgtatt tttagtagag atggggtttc      36240
accgtgttgt ccaggctcgt gtcaaacttc tgacctcaag ccatcccaccc gcctcggcct    36300 cccaaagtgc tgggattaca ggtgtgagcc accactcctg gccatgatag gttattttgt    36360
```

```
gatgaaaata cctacctctt aatttgtctg ataaatttaa attttatgtc tagatttcct   36420
aagatcagca cttccatatt ttaaagtaat ctgtatcaga ctaactgctc ttgcattctt   36480
ttaataccag tgactacttt gattcgtgaa acaatgtatt ttccttatga atagttttc    36540
tcatggtgta tttattcttt taagttttgt tttttaaata tacttcactt ttgaatgttt   36600
cagacagcag caaaagcagc aacagcagca gcagcagcag cagcagggg acctatcagg    36660
acagagttca catccatgtg aaaggccagc caccagttca ggagcacttg ggagtgatct   36720
aggtaaggcc tgctcaccat tcatcatgtt cgctaccttc acactttatc tgacatacga   36780
gctccatgtg atttttgctt tacattattc ttcattccct ctttaatcat attaagaatc   36840
ttaagtaaat ttgtaatcta ctaaatttcc ctggattaag gagcagttac caaaagaaaa   36900
aaaaaaaaaa aagctagatg tggtggctca catctgtaat cccagcactt ggggaaacca   36960
aggcaggaga ggattgctag aacatttaat gaatacttta acataataat ttaaacttca   37020
cagtaatttg tacagtctcc aaaaattcct tagacatcat ggatatttt ctttttttga    37080
gatggagtct tgctctgtca cccaggctgg agtgcagtgt cgcgatctcg gctcactgca   37140
agctctgctt cctgggttca tggcattctc ctgcctcagc ctcctgagta gctgggacta   37200
caggcgcccg ccacatcgcc tggctaattt tttgtatttt tagtagagac agggtttcac   37260
catgttagcc aggatggtct caatctcctg acctcatgat ccgcccgcct cggcctccca   37320
aagtgctggg attacaggcg tgagccatca cgtccggcca gaaatcatga atattagtag   37380
gtgaaaaata aacacatttt accacctgga aaatgaaaaa tacttgagta taatctaaat   37440
aacaatggga agtgcagagt tactttccag gtctcggttt aaatatgtct taaactttgg   37500
ccaattagta gtagaagttg agagaaaaag taactatctg acaaagaaat tataagcaga   37560
atatataaag aactcttaaa actgaataat cagaaaacaa ctcaataaaa aggtgaagga   37620
tttgaaaaga tatttcacca aataagacat agggatgaca aataagcaca tgaaaagact   37680
ctcagcatca ctagtcacag ggaaatgcac gataaaacca cagtgagaca ccatggcacc   37740
cctgtaggta tggctttaat gaagaaataa aactgacaat accaagtgtt ggcaaggatc   37800
caagcagctg agactcatat actgttaatg ggaatgtaaa agtgtacagc tttggaaaac   37860
agtttggcat ttttttgata aatgtatact tagccatgtg atccagcagt cccaatcatg   37920
tatatataac caaagaaaaa gaaaacttag gttcacataa aaacttatat caaatgctta   37980
tagctgacca ggcatggtgg cccatgccta taatcccagc actttgggag gccgaggttg   38040
gcagatacct gaagtcaagt gttcgagacc agcctggcca acatggcaaa accctgtctc   38100
tacttaaaat acaaaaatta gccaggcgtg atggcaggca cctgtagtcc agctattcag   38160
gaggctgagg caggagaatc acgtgaaccc gggaggcaga ggttgcagtg agccgagatc   38220
gtgccactat actccagcct gggtgacaga gcaaaactct gtctcaaaaa aaaaaaaaa    38280
aaaaagggct ggacacgtgg gcttacgcct gttatcccgg cactttggga ggccaaggct   38340
gatggatcac ctgaggtcag gagttcaaga ccagcctggc caacatggtg aaaccccatc   38400
tctactaaaa atacaaaaat ttgctgggca tggtggtggg cacctgtaat cccaggaggc   38460
tgaggcagga gaatcacttg aacccgggag gcggagattg cagtgagcca agattgtgcc   38520
attgaactcc agcctgggtg acaagaccaa aactccttct caaaaaaaaa aaagattata   38580
gcatctttat tcatcattgc ccaaaattac aaactgccta aatgtagacc ttcatttagt   38640
taatgaatgc acaaactgtg gtatatccaa acaattgaat aaaaaagga atgaactggt    38700
acttttttct attcctcctg tttaagtaca gccaaaacac ctcaacattt gtataaaaca   38760
```

```
tgagctgggc tgggtgcggt ggctcacacg tgtaatccca gcactttggg aggctgaggc   38820
gggtggatca cctaaggttg ggagttcaag accggtctga ccaacatgga gaaaccctgt   38880
ctcaactaaa aatacaagat tagtcgggca tggtggcgca tgcctgtaat cccagcttct   38940
tgggaggctg aggcaggaga attgcttgat cccgggaagc gaaggttgca gtaagctgag   39000
attgcaccat tgcactccag cctgggcaac aagagcaaaa ctctgtctca aaaagaaaaa   39060
aaaaaccatt cagctgaatc tcaaaggcag agagaagaca gactggctag ggaccttgga   39120
accagaggag cagtgtggtg gggagtggac tggattttct ttttgcctca tttatcctgg   39180
acttggtgct ggagaagcta tgggttcaga ccaagagaaa accccatgaa aagcctgctc   39240
tctctagcca aaagaggcaa cctagcaaga taaaaacctt tagataataa gcacttgact   39300
ccagtcaaac aaaacagaat aaactggccc cattcacccc tgtcagcaaa ggccaagtgg   39360
gagccaagat atgtacccca acctggaagt cataaggtac acttctcccc tttcccagcc   39420
aaggtggtgt tagagaaggc tgactgggga gctgggattc tcattccctc caggaggtga   39480
taacactcct ttcacatggt gtcagtggtc acagggaggc tgaacttcca cccagtaata   39540
cataggcatc tctctggctc ctatatgggt gatgttggag aagaggccga gtagagaatc   39600
cagactgttg ctgacaccca gcagtaacaa ggacacctcc acaatgtccg tggaggccat   39660
gtggagatca gtaacaaggc actgctctcc ctcccagtca gagagatgtc agtggaggac   39720 taggggcta gaactcccat gtgcgttcag cagtaatccc catgaccgcc actccttgac   39780
atcacaggcc ttgaagaaac ctggactttc actcccctct ggttgtagcg aggtggcact   39840
cccttttccc tgttgccagt gctgtgtcag tggaggcttg ctaaattgga agatgtaaat   39900
aagattcaca ttctcataac ataatacccc aaattttcag gatttaattg aaaatcacta   39960
agctgggcat ggtggctcac acctgtaatc ccagcacttt ggggaggccaa ggtgggccaa   40020 acacttaagg tcaggaattc aagaccagcc tggccagcat ggtgaaaccc tgtctctact   40080
aaaaatacaa aaattagctg gcgtggtgg cacatgcctg taatcccagc tactgggaag   40140
gctaaggcag gaaaatcact ggaacctggg agacggaggt tgcagtgatc caagatcgca   40200
ctagtgtact gcagcctggg caacagagca agactccatc taaatttgtg tcaggattcc   40260
cagaaggaga tgagaaggg tggggctgaa aaaaattgag gaagaagtca tggctgaaaa   40320
tttcccaaat ttggcaaaag tcagaaacct acagattgaa aaagctgaat gaagctcaaa   40380
tatgataaac tcaaagaagt tcacacagag acacatcaca gtcagatttc tgaacactgc   40440
agacaaaaaa tgaagatctc gaaattagca agaaatgacc ttacctaagc aatttgaatg   40500
acagcagatt tcccatcaga gatcataaag gccagaagga aggggtacat acaacatttt   40560
ttctagtgct gaaagacaaa aactctaggc tgggcacggt ggcacacacc tgtaatccca   40620
gcacttttgg aggctgaggc aggcagatca cctgaagtca ggagttcgag accagcctgg   40680
ccaacatggg gaaaccctgt ctctactaaa aatacaaaaa ttagccaggt gtggtggcac   40740
gcacctataa tcctagctac ttgggaggct gaggcagggg aatcgcttga acctgggagg   40800
cgacggttgc agtgagccaa ggtcgcgcca ctgcactcca gcctgggcag ttgagcgaga   40860
ctccatctca aaaaaaaaa aattatccag gcttggtggt gggcgcctat agtcccagct   40920
acttgggagg ctgaggcaag agaattggtt gaacccagga ggtggaggtt gcagtgagcc   40980
aagctcatgc cactgtactc cagcctgggt gacagagcga gccttgtct caaaaaaaaa   41040 aaaaaaaaaa aaaacaaga aaaaactct aaacccagag ttacatatcc agtgaaatat   41100
```

```
ccttcaggag tgaagggaaa attaacgatt tgtcttcagg agacctaccc taaaagaatg    41160
gctaaaggaa tttctctaaa cagaaaagaa atgataaaag aagtaatttt ggaacatcag    41220
gaaggaagaa agaacaataa aaagagtaaa atatgggtaa acacaataga ctttcccctc    41280
cttttgaatt ttctaaattg tatgatggtt gaagcaagaa ttatagcact gatttggttt    41340
tcagtatata tattggaaat atttaaggca ttatgttaca gatgaaggag ggtcaaagga    41400
tataagggga ggtaaccttt ctatatttct tttgtactga tgcaggcact ttggaaaata    41460
atttcactat ttgtttaaaa actgaacata ccctgaccat atgacatagc atctatactc    41520
ctgggcattt atcccagaga aacagaaatt tatttatttt tttttttagta ttacactccg    41580 taagtgctgt aatactagca cttagggagg ctgaggcaag cagattgctt gagcccagga    41640
gttcaagacc agcctgggca atgctgcaca gtcaaaaaag aaaaacaaac atttagaaaa    41700
ctattttaaa agtctttaat tgctgaatgc ctctttggct aatatttgga agatcattat    41760
tattattttt ctttttttagg cagagtcttg ctctgtcact gaggctggag tgcagtggcg    41820
ccatctcggc ttactgcaac ctctgcctcc cgggttcacg ccattctcct gcctcagcct    41880
cccgagtagc tgggactaca ggcgtgtgcc accatgcccg gctaattttt tgtgttttta    41940
gtagagatgg ggtttcacta tgttagtcag gatggtctcc atctcctaac ctcgtgatcc    42000
gcccacctcg gcttcccaaa atgctgggat tacaggcgtg agccactgtg cccagcctgg    42060
aagatcatta tttagtccta caactgacac attgttccac tgacgcaatt gcccaggctg    42120
gtcttgaact cctgggctca agcaatctgc ctgcctcggc ctccctaagt gctagtatta    42180
caggcttgag ccactgtgcc cagccaaaaa tagaaattta tattctcaca aaaacatgta    42240
catgaatgtt tatagcagct ttacttgtca taatcaaaaa ctggaaacaa ccaaaatgtc    42300
ctacagtgaa acaaactgta gtacatccat agcatgtaat actctactgt caggattaaa    42360
aagaaaccca ctgttggcac aggcagcacc gtggctggat ctcagggggca ttatgctgag    42420 tgcaaaaaag cctcaaaggg tcttacactg tatgattcca cttgttcaac taaaaatgac    42480
agctgtatag agatagagaa catattagtg gtttccacta gttagagaaa gtgggtaaaa    42540
gataggtggg tgggaatata atcgatagc agggagatct ttgtggtatt ataacacttc    42600
tatgtcttga ttgtagtggt ggtggttaca tgaatacacg tgtgataaaa tgccatgtag    42660
aactacatat aacgttgtgc caatgtcaat atctaggttt tagtttgatc tttagttaca    42720
taagatgtaa ctattgggtg aaattgggca aaagagtaca cgaaacctct cttaaatatc    42780
tttacaactt ccctttgaatt gacagttttt caaaatagaa agttgggttt ttgtaaatac    42840
atgaattgtt gatatacaca acaaatctca aatgcattat gctacgtgaa agaagccata    42900
ttcaaaaggc tacataccta ctgatgcctt ttatatgacg tgcaggaaaa gataaaactg    42960
taggacagag aatatactgg tggctatctg ggattaggaa atggggatcg accacaaagg    43020
ggcagcatgg gggaattttc tggggcaatg gaatggttgt gtatcttgat ggtgtatttg    43080
tcaaaatata tagaactata aaagtaaatt ttgctttata tgtattaaat caaaaaaga    43140 aactcgtgct caaatagaaa tacatttttct gagaacttgc cttttgatga ctttgagaat    43200
tttctggaaa ttttaaagaa atgtggtttt gtttcccaac aggtgatgct atgagtgaag    43260
aagacatgct tcaggcagct gtgaccatgt ctttagaaac tgtcagaaat gatttgaaaa    43320
cagaaggaaa aaaataatac ctttaaaaaa taatttagat attcatactt ccaacatta    43380 tcctgtgtga ttacagcata gggtccactt tggtaatgtg tcaaagagat gaggaaataa    43440 gactttagc ggtttgcaaa caaaatgatg ggaaagtgga acaatgcgtc ggttgtagga    43500
```

```
ctaaataatg atcttccaaa tattagccaa agaggcattc agcaattaaa gacatttaaa   43560
atagttttct aaatgtttct ttttcttttt tgagtgtgca atatgtaaca tgtctaaagt   43620
tagggcattt ttcttggatc tttttgcaga ctagctaatt agctctcgcc tcaggctttt   43680
tccatatagt ttgttttctt tttctgtctt gtaggtaagt tggctcacat catgtaatag   43740
tggctttcat ttcttattaa ccaaattaac ctttcaggaa agtatctcta ctttcctgat   43800
gttgataata gtaatggttc tagaaggatg aacagttctc ccttcaactg tataccgtgt   43860
gctccagtgt tttcttgtgt tgttttctct gatcacaact tttctgctac ctggttttca   43920
ttattttccc acaattcttt tgaaagatgg taatctcttc tgaggtttag cgttttaagc   43980
cctacgatgg gatcattatt tcatgactgg tgcgttccta aactctgaaa tcagccttgc   44040
acaagtactt gagaataaat gagcatttt  taaaatgtgt gagcatgtgc tttcccagat   44100
gctttatgaa tgtcttttca cttatatcaa aaccttacag ctttgttgca accccttctt   44160
cctgcgcctt attttttcct ttcttctcca attgagaaaa ctaggagaag catagtatgc   44220
aggcaagtct ccttctgtta gaagactaaa catacgtacc caccatgaat gtatgataca   44280
tgaaatttgg ccttcaattt taatagcagt tttattttat ttttctcct  atgactggag   44340 ctttgtgttc tctttacagt tgagtcatgg aatgtaggtg tctgcttcac atctttttagt  44400 aggtatagct tgtcaaagat ggtgatctgg aacatgaaaa taatttacta atgaaaatat   44460
gtttaaattt atactgtgat ttgacacttg catcatgttt agatagctta agaacaatgg   44520
aagtcacagt acttagtgga tctataaata agaaagtcca tagttttgat aaatattctc   44580
tttaattgag atgtacagag agtttcttgc tgggtcaata ggatagtatc attttggtga   44640
aaaccatgtc tctgaaattg atgttttagt ttcagtgttc cctatccctc attctccatc   44700 tcctttgaa  gctcttttga atgttgaatt gttcataagc taaaatccaa gaaatttcag   44760
ctgacaactt cgaaaattat aatatggtat attgccctcc tggtgtgtgg ctgcacacat   44820
tttatcaggg aaagttttt  gatctaggat ttattgctaa ctaactgaaa agagaagaaa   44880
aaatatcttt tatttatgat tataaaatag ctttttcttc gatataacag attttttaag   44940
tcattatttt gtgccaatca gttttctgaa gtttccctta cacaaaagga tagctttatt   45000
ttaaaatcta aagtttcttt taatagttaa aaatgtttca gaagaattat aaaactttaa   45060
aactgcaagg gatgttggag tttagtacta ctccctcaag atttaaaaag ctaaatattt   45120
taagactgaa catttatgtt aattattacc agtgtgtttg tcatattttc catggatatt   45180
tgttcattac cttttttccat tgaaaagtta cattaaactt ttcatacact tgaattgatg   45240
agctacctaa tataaaaatg agaaaaccaa tatgcatttt aaagttttaa ctttagagtt   45300
tataaagttc atatataccc tagttaaagc acttaagaaa atatggcatg tttgactttt   45360
agttcctaga gagttttgt  tttgttttt  gtttttttt  gagacggagt cttgctatgt   45420
ctcccaggct ggagggcagt ggcatgatct cggctcacta caacttccac ctcccggtt    45480 caagcaattc tcctgcctca gcctccagag tagctgggat tacaggcgcc caccaccaca   45540
cccggcagat ttttgtattt ttggtagaga cgcggtttca tcatgtttgg ccaggctggt   45600
ctcgaactcc tgacctcagg tgatccgcct gccttggcct cccaaagtgt gggattaca    45660 ggcatgagcc actgcgcctg gccagctaga gagtttttaa agcagagctg agcacacact   45720
ggatgcgttt gaatgtgttt gtgtagtttg ttgtgaaatt gttacattta gcaggcgat    45780 ccagaagcac tagtgaactg tcatcttggt ggggttggct taaatttaat tgactgttta   45840
```

```
gattccattt cttaattgat tggccagtat gaaaagatgc cagtgcaagt aaccatagta   45900
tcaaaaaagt taaaaattat tcaaagctat agtttataca tcaggtactg ccatttactg   45960
taaaccacct gcaagaaagt caggaacaac taaattcaca agaactgtcc tgctaagaag   46020
tgtattaaag atttccattt tgttttacta attgggaaca tcttaatgtt taatatttaa   46080
actattggta tcattttcct aatgtataat ttgtattact gggatcaagt atgtacagtg   46140
gtgatgctag tagaagttta agccttggaa ataccacttt catattttca gatgtcatgg   46200
atttaatgag taatttatgt ttttaaaatt cagaatagtt aatctctgat ctaaaaccat   46260
caatctatgt ttttacggt aatcatgtaa atatttcagt aatataaact gtttgaaaag   46320
gctgctgcag gtaaactcta tactaggatc ttggccaaat aatttacaat tcacagaata   46380
ttttatttaa ggtggtgctt ttttttttg tccttaaaac ttgattttc ttaacttat   46440 tcatgatgcc aaagtaaatg aggaaaaaaa ctcaaaacca gttgagtatc attgcagaca   46500
aaactaccag tagtccatat tgtttaatat taagttgaat aaaataaatt ttatttcagt   46560
cagagcctaa atcacatttt gattgtctga attttgata ctattttaa aatcatgcta   46620 gtggcggctg ggcgtggtag ctcacgcctg taatcccagc attttgggag gccgaagtgg   46680
gtggatcacg aggtcgggag ttcgagacca gcttggccaa aatggtgaaa ccccatctgt   46740
actaaaaact acaaaaatta gctgggcgcg gtggcaggtg cctgtaatcc cagctacctg   46800
ggagtctgag gcaggagaat tgcttgaacc ctggcgacag aggatgcagt gagccaagat   46860
ggtgccactg tactccagac tgggcgacag agtgagactc tgtctcaaaa aaaaaaaaa   46920 aatcatgcta gtgccaagag ctactaaatt cttaaaaccg gcccattgga cctgtacaga   46980
taaaaaatag attcagtgca taatcaaaat atgataattt taaaatctta agtagaaaaa   47040
taaatcttga tgttttaaat tcttacgagg attcaatagt taatattgat gatctcccgg   47100
ctgggtgcag tggctcacgc ctgtaatccc agcagttctg gaggctgagg tgggcgaatc   47160
acttcaggcc aggagttcaa gaccagtctg gcaacatgg tgaaacctcg tttctactaa   47220
aaatacaaaa attagccggg cgtggttgca cacttgta atcccagcta ctcaggaggc   47280
taagaatcgc atgagcctag gaggcagagg ttgcagagtg ccaagggctc accactgcat   47340
tccagcctgc ccaacagagt gagacactgt ttctgaaaaa aaaaaatata tatatatata   47400
tatatatgtg tgtatatata tatgtatata tatgacctt cctattaaaa actttatccc   47460
agtcgggggc agtggctcac gcctgtaatc ccaacacttt gggaggctga ggcaggtgga   47520
tcacctgaag tccggagttt gagaccagcc tggccaacat ggtgaaaccc catctctact   47580
aaaaatacaa aacttaagcc aggtatggtg gcgggcacct gtaatcccag ttacttggga   47640
ggctgaggca ggagaatcgt ttaaacccag gaggtggagg ttgcagtgag ctgagatcgt   47700
gccattgcac tctagcctgg gcaacaagag taaaactcca tcttaaaggt tgtttgttt   47760 ttttttaatc cggaaacgaa gaggcgttgg gccgctattt tcttttttctt tctttctttc   47820 tttcttttt ttttttttctg agacggagtc tagctctgct gcccaggctg gagtacaatg   47880
acacgatgtt ggctcactgc aacctccacc tcctgggttc aagcgattct cctgcctcag   47940
cctcccaagt acctgggatt acaggcacct gccactacac ctggcgaata tttgtttttt   48000
ttagtagaga cgggctttta ccatgttagg ctggtctcaa actcctgacc tcaggtgatc   48060
tgcctgcctt ggcctcccaa agtgctggga ttacaggtgc aggccaccac acccggcctt   48120
gggccactgt tttcaaagtg aattgttgt tgtatcgagt ccttaagtat ggatatatat   48180
gtgaccctaa ttaagaacta ccagattgga tcaactaatc atgtcagcaa tgtaaataac   48240
```

```
tttattttc  atattcaaaa  taaaaacttt  cttttatttc  tggcccttt   ataaccagca  48300
tcttttgct   ttaaaaaatg  acctggcttt  gtattttttt  agtcttaaac  ataataaaaa  48360
tatttttgtt  ctaatttgct  ttcatgagtg  aagattattg  acatcgttgg  taaattctag  48420
aattttgatt  ttgtttttta  atttgaagaa  atctttgct   attattattt  tttccaagtg  48480
gtctggcatt  ttaagaatta  gtgctaataa  cgtaacttct  aaatttgtcg  taattggcat  48540
gtttaatagc  atatcaaaaa  acattttaag  cctgtggatt  catagacaaa  gcaatgaaa   48600
acattagtaa  aatataaatg  gatattcctg  atgcatttag  gaagctctca  attgtctctt  48660
gcatagttca  aggaatgttt  tctgaatttt  tttaatgctt  ttttttttt   tgaaagagga  48720
aaacatacat  ttttaaatgt  gattatctaa  tttttacaac  actgggctat  taggaataac  48780
ttttaaaaa   ttactgttct  gtataaatat  ttgaaattca  agtacagaaa  atatctgaaa  48840
caaaaagcat  tgttgtttgg  ccatgataca  agtgcactgt  ggcagtgccg  cttgctcagg  48900
acccagccct  gcagcccttc  tgtgtgtgct  ccctcgttaa  gttcatttgc  tgttattaca  48960
cacacaggcc  ttcctgtctg  gtcgttagaa  aagccgggct  tccaaagcac  tgttgaacac  49020
aggattctgt  tgttagtgtg  gatgttcaat  gagttgtatt  ttaaatatca  aagattatta  49080
aataaagata  atgtttgctt  ttctatttcc  ttttgaattt  gtgtttattg  ttaattcata  49140
gctattcaaa  gtgtgattag  agctgggctt  ggtggcttgc  atctacagtt  ccagctaccc  49200
aggaggcaga  agcaggagga  ttgcttgagc  ctaggagttc  gaggctgcag  tgagctatga  49260
tcctgccact  gaattctagc  ctgggcgaca  aaacaggaaa  aaagtatgga  tggaggacca  49320
gcagcatctg  tatcacctgt  gagtctttca  gaaatgcaga  gtttcaggct  acactcggac  49380
ctactgaatc  agaacttgca  cttttacaa   gatccccagg  acactaaagt  atagagtgaa  49440
gcttgagaag  cgctgttgtg  tggattgttc  ttaaccagct  gcagtgatga  atatgaataa  49500
cgcaggccag  cacagtccat  tgatattcta  ttccagctta  ctgcctgcca  aaaggtccat  49560
tattactgga  tcctcagtct  tttccaagag  aagctaagaa  ttccaaatt   ttatttgaaa  49620
tatatttttt  aaatgtttgt  tcaactggcc  cagtgccagt  ggctcatgcc  tttaatccta  49680
gcactttgag  aggccgaggt  ggaaggatca  cttgacccca  ggagtttgag  accagcctgg  49740
gcaacataaa  gagacccat   ctctattaaa  aaaaaataga  gacaatgctg  ccttaaaaaa  49800
gtcaaataaa  tgtttgctca  actgatttt   aatactgagg  gccaaacaaa  gcacatcaaa  49860
tttttaagtg  ctgctttcc   tcattttatc  caactctgga  caccagaatc  caaatgtagt  49920
gattggaatc  cacctagact  gattgaggaa  tatattgtcc  tcaaatttta  tgagggttga  49980
ctattcattt  taactttaat  t                                               50001
```

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ccataaaaca gacctggaac g                                                 21

<210> SEQ ID NO 3
<211> LENGTH: 20
<212> TYPE: DNA
<213> ORGANISM: Artificial sequence
<220> FEATURE:

<223> OTHER INFORMATION: Primer

<400> SEQUENCE: 3
cgcattgttc cactttccca                                              20

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
gctgttgctg cttttgctgc tg                                           22

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ctgttgctgc ttttgctgct                                              20

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
gagatatgtt tctggaacta cc                                           22

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
gcttctcgtc tcttccgaag c                                            21

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ccgaagctct tctgaagtaa                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
gaactctgtc ctgataggtc                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ctagatcact cccaagtgct                                               20

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
ataggtcccg ctgctgct                                                 18

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
gctgttgctg cttttgctgc tg                                            22

<210> SEQ ID NO 13
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 13
gcuucucguc ucuuccgaag c                                             21

<210> SEQ ID NO 14
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 14
gcuguugcug cuuuugcugc ug                                            22

<210> SEQ ID NO 15
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 15
cugaacuggu cuacagcuc                                                19